(12) United States Patent
Wilson et al.

(10) Patent No.: US 8,506,623 B2
(45) Date of Patent: Aug. 13, 2013

(54) IMPLANT DELIVERY AND DEPLOYMENT SYSTEM AND METHOD

(75) Inventors: Jonathan E. Wilson, Amesbury, MA (US); Robert J. St. John, Mansfield, MA (US); Stephen R. Polgar, Taunton, MA (US)

(73) Assignee: Cardiosolutions, Inc., Stoughton, MA (US)

( * ) Notice: Subject to any disclaimer, the term of this patent is extended or adjusted under 35 U.S.C. 154(b) by 0 days.

(21) Appl. No.: 13/545,927

(22) Filed: Jul. 10, 2012

(65) Prior Publication Data

US 2013/0041459 A1 Feb. 14, 2013

Related U.S. Application Data

(63) Continuation of application No. 12/431,399, filed on Apr. 28, 2009, now Pat. No. 8,216,302, which is a continuation-in-part of application No. 11/258,828, filed on Oct. 26, 2005, now Pat. No. 8,092,525, and a continuation-in-part of application No. 11/940,694, filed on Nov. 15, 2007, and a continuation-in-part of application No. 12/209,686, filed on Sep. 12, 2008.

(51) Int. Cl.
*A61F 2/24* (2006.01)

(52) U.S. Cl.
USPC ........................................................ 623/2.11

(58) Field of Classification Search
None
See application file for complete search history.

(56) References Cited

U.S. PATENT DOCUMENTS

| | | | |
|---|---|---|---|
| 2,549,731 A | 4/1951 | Wattley |
| 2,625,967 A | 1/1953 | Stull |
| 3,197,788 A | 8/1965 | Segger |
| 3,445,916 A | 5/1969 | Schulte |
| 3,551,913 A | 1/1971 | Shiley et al. |

(Continued)

FOREIGN PATENT DOCUMENTS

| EP | 0125393 | 11/1984 |
|---|---|---|
| EP | 1323438 | 2/2003 |

(Continued)

OTHER PUBLICATIONS

Canadian Office Action dated Sep. 18, 2012 issued in Canadian Patent Application No. 2,627,517, 2 pages.

(Continued)

*Primary Examiner* — Melanie Tyson
*Assistant Examiner* — Son Dang
(74) *Attorney, Agent, or Firm* — Grossman Tucker Perreault & Pfleger PLLC

(57) ABSTRACT

An implant delivery system comprising a catheter including at least one lumen, an implant configured for receipt in the lumen, and a latching mechanism configured for receipt in the implant. The latching mechanism may be configured to releasably couple the implant to a delivery wire and to transmit torque through the delivery wire to cause at least a portion of the implant to rotate. The an implant may comprise a shaft, a spacer configured to interact with at least a portion of at least one cusp of a heart valve to at least partially restrict a flow of blood through the heart valve in a closed position, a garage configured to couple the spacer to a first end region of the shaft, and at least one anchor mechanism. The garage may define a cavity to receive the latching mechanism and to increase rotational and translational stability of the latching mechanism.

10 Claims, 12 Drawing Sheets

(56) References Cited

U.S. PATENT DOCUMENTS

| | | |
|---|---|---|
| 3,586,029 A | 6/1971 | Evers |
| 3,589,392 A | 6/1971 | Meyer |
| 3,671,979 A | 6/1972 | Moulopoulos |
| 3,689,942 A | 9/1972 | Rapp |
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Ionescu et al. |
| 4,259,753 A | 4/1981 | Liotta et al. |
| 4,291,420 A | 9/1981 | Reul |
| 4,297,749 A | 11/1981 | Davis et al. |
| 4,439,185 A | 3/1984 | Lundquist |
| 4,535,757 A | 8/1985 | Webster, Jr. |
| 4,597,767 A | 7/1986 | Lenkei |
| 4,865,030 A | 9/1989 | Polyak |
| 4,960,424 A | 10/1990 | Grooters |
| 5,002,067 A * | 3/1991 | Berthelsen et al. ........... 607/120 |
| 5,217,484 A | 6/1993 | Marks |
| 5,222,973 A | 6/1993 | Sharpe et al. |
| 5,261,916 A | 11/1993 | Engelson |
| 5,304,195 A | 4/1994 | Twyford, Jr. et al. |
| 5,308,357 A | 5/1994 | Lichtman |
| 5,318,589 A | 6/1994 | Lichtman |
| 5,350,397 A | 9/1994 | Palermo et al. |
| 5,397,351 A | 3/1995 | Pavcnik et al. |
| 5,411,552 A | 5/1995 | Andersen et al. |
| 5,415,667 A | 5/1995 | Frater |
| 5,462,527 A | 10/1995 | Stevens-Wright et al. |
| 5,509,428 A | 4/1996 | Dunlop |
| 5,582,607 A | 12/1996 | Lackman |
| 5,611,800 A | 3/1997 | Davis et al. |
| 5,634,936 A | 6/1997 | Linden et al. |
| 5,638,827 A | 6/1997 | Palmer et al. |
| 5,649,949 A | 7/1997 | Wallace et al. |
| 5,653,712 A | 8/1997 | Stern |
| 5,665,100 A | 9/1997 | Yoon |
| 5,776,075 A | 7/1998 | Palmer |
| 5,792,179 A | 8/1998 | Sideris |
| 5,797,958 A | 8/1998 | Yoon |
| 5,814,098 A | 9/1998 | Hinnenkamp et al. |
| 5,840,081 A | 11/1998 | Andersen et al. |
| 5,891,130 A | 4/1999 | Palermo et al. |
| 5,895,391 A | 4/1999 | Farnholtz |
| 5,928,224 A | 7/1999 | Laufer |
| 5,957,865 A | 9/1999 | Backman et al. |
| 5,957,949 A | 9/1999 | Leonhardt et al. |
| 5,989,242 A | 11/1999 | Saadat et al. |
| 5,993,474 A | 11/1999 | Ouchi |
| 6,090,096 A | 7/2000 | St. Goar et al. |
| 6,152,144 A | 11/2000 | Lesh et al. |
| 6,168,614 B1 | 1/2001 | Andersen et al. |
| 6,190,373 B1 | 2/2001 | Palermo et al. |
| 6,217,610 B1 | 4/2001 | Carpentier et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,332,893 B1 | 12/2001 | Mortier et al. |
| 6,358,277 B1 | 3/2002 | Duran |
| 6,415,693 B1 | 7/2002 | Simon et al. |
| 6,419,695 B1 | 7/2002 | Gabbay |
| 6,440,132 B1 | 8/2002 | Jackson |
| 6,454,798 B1 | 9/2002 | Moe |
| 6,461,382 B1 | 10/2002 | Cao |
| 6,482,228 B1 | 11/2002 | Norred |
| 6,508,825 B1 | 1/2003 | Selmon et al. |
| 6,592,606 B2 | 7/2003 | Huter et al. |
| 6,652,578 B2 | 11/2003 | Bailey et al. |
| 6,673,100 B2 | 1/2004 | Diaz et al. |
| 6,682,559 B2 | 1/2004 | Myers et al. |
| 6,695,866 B1 | 2/2004 | Kuehn et al. |
| 6,746,404 B2 | 6/2004 | Schwartz |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,821,297 B2 | 11/2004 | Snyders |
| 6,830,584 B1 | 12/2004 | Seguin |
| 6,830,585 B1 | 12/2004 | Artof et al. |
| 6,849,081 B2 | 2/2005 | Sepetka et al. |
| 6,869,444 B2 | 3/2005 | Gabbay |
| 6,896,700 B2 | 5/2005 | Lu et al. |
| 6,911,043 B2 | 6/2005 | Myers et al. |
| 6,971,998 B2 | 12/2005 | Rosenman et al. |
| 6,974,476 B2 | 12/2005 | McGuckin, Jr. et al. |
| 7,018,406 B2 | 3/2006 | Seguin et al. |
| 7,056,286 B2 | 6/2006 | Ravenscroft et al. |
| 7,070,618 B2 | 7/2006 | Streeter |
| 7,077,862 B2 | 7/2006 | Vidlund et al. |
| 7,101,395 B2 | 9/2006 | Tremulis et al. |
| 7,112,219 B2 | 9/2006 | Vidlund et al. |
| 7,160,322 B2 | 1/2007 | Gabbay |
| 7,189,199 B2 | 3/2007 | McCarthy et al. |
| 7,247,134 B2 | 7/2007 | Vidlund et al. |
| 7,344,553 B2 | 3/2008 | Opolski et al. |
| 7,374,572 B2 | 5/2008 | Gabbay |
| 7,381,210 B2 | 6/2008 | Zarbatany et al. |
| 7,404,824 B1 | 7/2008 | Webler et al. |
| 7,657,326 B2 * | 2/2010 | Bodner et al. ................. 607/127 |
| 7,678,145 B2 | 3/2010 | Vidlund et al. |
| 7,753,949 B2 | 7/2010 | Lamphere et al. |
| 7,785,366 B2 | 8/2010 | Maurer et al. |
| 8,092,525 B2 | 1/2012 | Eliasen et al. |
| 8,216,302 B2 | 7/2012 | Wilson et al. |
| 2001/0007956 A1 | 7/2001 | Letac et al. |
| 2001/0010017 A1 | 7/2001 | Cribier et al. |
| 2002/0042651 A1 | 4/2002 | Liddicoat et al. |
| 2002/0058995 A1 | 5/2002 | Stevens |
| 2002/0077566 A1 | 6/2002 | Laroya et al. |
| 2002/0081553 A1 | 6/2002 | Tramonte |
| 2002/0183838 A1 | 12/2002 | Liddicoat et al. |
| 2002/0188170 A1 | 12/2002 | Santamore et al. |
| 2003/0033009 A1 | 2/2003 | Gabbay |
| 2003/0040792 A1 | 2/2003 | Gabbay |
| 2003/0105519 A1 | 6/2003 | Fasol et al. |
| 2003/0130731 A1 | 7/2003 | Vidlund et al. |
| 2003/0139751 A1 | 7/2003 | Evans et al. |
| 2003/0144574 A1 | 7/2003 | Heilman et al. |
| 2003/0181945 A1 | 9/2003 | Opolski et al. |
| 2003/0199975 A1 | 10/2003 | Gabbay |
| 2003/0208203 A1 | 11/2003 | Lim et al. |
| 2003/0212453 A1 | 11/2003 | Mathis et al. |
| 2004/0034366 A1 | 2/2004 | van der Burg et al. |
| 2004/0044402 A1 | 3/2004 | Jung et al. |
| 2004/0088047 A1 | 5/2004 | Spence et al. |
| 2004/0106989 A1 | 6/2004 | Wilson et al. |
| 2004/0122512 A1 | 6/2004 | Navia et al. |
| 2004/0127981 A1 | 7/2004 | Rahdert et al. |
| 2004/0127983 A1 | 7/2004 | Mortier et al. |
| 2004/0148020 A1 | 7/2004 | Vidlund et al. |
| 2004/0181256 A1 | 9/2004 | Glaser |
| 2004/0210304 A1 | 10/2004 | Seguin et al. |
| 2004/0210307 A1 | 10/2004 | Khairkhahan |
| 2004/0225353 A1 | 11/2004 | McGuckin, Jr. et al. |
| 2004/0225354 A1 | 11/2004 | Allen et al. |
| 2004/0243229 A1 | 12/2004 | Vidlund et al. |
| 2005/0021056 A1 | 1/2005 | St. Goar et al. |
| 2005/0033446 A1 | 2/2005 | Deem et al. |
| 2005/0038508 A1 | 2/2005 | Gabbay |
| 2005/0038509 A1 | 2/2005 | Ashe |
| 2005/0065591 A1 | 3/2005 | Moberg et al. |
| 2005/0070999 A1 | 3/2005 | Spence |
| 2005/0075727 A1 | 4/2005 | Wheatley |
| 2005/0090824 A1 | 4/2005 | Shluzas et al. |
| 2005/0131451 A1 | 6/2005 | Kleshinski et al. |
| 2005/0159810 A1 | 7/2005 | Filsoufi |
| 2005/0222488 A1 | 10/2005 | Chang et al. |
| 2005/0288786 A1 | 12/2005 | Chanduszko |
| 2006/0025855 A1 | 2/2006 | Lashinski et al. |
| 2006/0058871 A1 | 3/2006 | Zakay et al. |
| 2006/0084943 A1 | 4/2006 | Rosenman et al. |
| 2006/0129025 A1 | 6/2006 | Levine et al. |
| 2006/0149368 A1 | 7/2006 | Spence |
| 2006/0155326 A1 | 7/2006 | Aranyi |

| | | | |
|---|---|---|---|
| 2006/0178700 A1 | 8/2006 | Quinn | |
| 2006/0195012 A1 | 8/2006 | Mortier et al. | |
| 2006/0195185 A1 | 8/2006 | Lane et al. | |
| 2006/0199995 A1 | 9/2006 | Vijay | |
| 2006/0229708 A1 | 10/2006 | Powell et al. | |
| 2006/0241745 A1 | 10/2006 | Solem | |
| 2006/0253072 A1 | 11/2006 | Pai et al. | |
| 2006/0293698 A1 | 12/2006 | Douk | |
| 2007/0049980 A1 | 3/2007 | Zielinski et al. | |
| 2007/0093890 A1 | 4/2007 | Eliasen et al. | |
| 2007/0118151 A1 | 5/2007 | Davidson | |
| 2007/0167981 A1 | 7/2007 | Opolski et al. | |
| 2007/0185571 A1 | 8/2007 | Kapadia et al. | |
| 2007/0198050 A1 | 8/2007 | Ravenscroft et al. | |
| 2007/0198082 A1 | 8/2007 | Kapadia et al. | |
| 2007/0213578 A1 | 9/2007 | Khairkhahan et al. | |
| 2007/0232981 A1 | 10/2007 | Ravenscroft et al. | |
| 2007/0239154 A1 | 10/2007 | Shaolian et al. | |
| 2007/0255399 A1 | 11/2007 | Eliasen et al. | |
| 2007/0265700 A1 | 11/2007 | Eliasen et al. | |
| 2007/0282429 A1 | 12/2007 | Hauser et al. | |
| 2007/0293943 A1 | 12/2007 | Quinn | |
| 2008/0125860 A1 | 5/2008 | Webler et al. | |
| 2008/0125861 A1 | 5/2008 | Webler et al. | |
| 2008/0183105 A1 | 7/2008 | Greenhalgh et al. | |
| 2008/0195200 A1 | 8/2008 | Vidlund et al. | |
| 2008/0288061 A1 | 11/2008 | Maurer et al. | |
| 2009/0043382 A1 | 2/2009 | Maurer et al. | |
| 2009/0048668 A1 | 2/2009 | Wilson et al. | |
| 2009/0105814 A1 | 4/2009 | Groothuis et al. | |
| 2009/0131849 A1 | 5/2009 | Maurer et al. | |
| 2009/0131880 A1 | 5/2009 | Speziali et al. | |
| 2009/0132033 A1 | 5/2009 | Maurer et al. | |
| 2009/0163934 A1 | 6/2009 | Raschdorf, Jr. et al. | |
| 2009/0240326 A1 | 9/2009 | Wilson et al. | |
| 2010/0022948 A1 | 1/2010 | Wilson et al. | |
| 2010/0324668 A1 | 12/2010 | Maurer et al. | |
| 2012/0143320 A1 | 6/2012 | Eliasen et al. | |

FOREIGN PATENT DOCUMENTS

| | | |
|---|---|---|
| GB | 1264472 | 2/1972 |
| GB | 1268484 | 3/1972 |
| GB | 1388064 | 3/1975 |
| WO | 03/049619 | 6/2003 |
| WO | WO2006032051 | 3/2006 |
| WO | 2006/064490 | 6/2006 |
| WO | 2006091597 | 8/2006 |
| WO | 2006/111391 | 10/2006 |
| WO | 2006127509 | 11/2006 |
| WO | 2007064810 | 6/2007 |
| WO | 2007078772 | 7/2007 |
| WO | 2007100409 | 9/2007 |
| WO | 2007/140470 | 12/2007 |
| WO | 2008079828 | 7/2008 |
| WO | 2009053952 | 4/2009 |

OTHER PUBLICATIONS

Intent to Grant dated Jan. 2, 2013 issued in European Patent Application No. 06816336.9, 7 pages.
Notice of Allowance dated Jan. 9, 2013 issued in U.S. Appl. No. 11/748,121, 7 pages.
Bailey et al, "Surgical Repair of Mitral Insufficiency" Feb. 1951 (pp. 125-137 ).
Bailey et al, "Closed Intracardiac Tactile Surgery" Jul. 1952 (pp. 1-24).
Bailey et al., "The Surgical Correction of Mitral Insufficiency by the Use of Pericardial Grafts" Dec. 1954 (pp. 551-627).
Benichoux et al., "A Method of Surgical Correction of Mitral Insufficiency" 1955 (pp. 148-158).
Blalock, "A Consideration of Some of the Problems in Cardiovascular Surgery" Jun. 1951 (pp. 543-571).
Borrie, "Mitral Insufficiency: Experimental Circular Suture Around the Artioventricular Ring" 1955 (pp. 687-697).
Carter et al. "Surgical Treatment of Mitral Insufficiency" 1953 (pp. 574-583).
European Search Report dated Jul. 12, 1984 cited in EP0125393.
"French catheter scale chart" http://en.wikipedia.org/wiki/French_catheter_scale_chart, Dec. 20, 2006, 1 page.
"General Physical Properties of PVA Sponge (values are not guaranteed)", Ceiba Technologies, http://www.ceibatech.com/PVASpongeDate.htm, Dec. 20, 2006 3 pages.
Glenn et al., "The Implantation of a Vascularized Graft in the Chambers of the Heart" 1954 (pp. 5-11).
Glenn et al, "The Surgical Treatment of Mitral Insufficiency: the Fate of Vascularized Transchamber Intracardiac Graft" Apr. 1955 (pp. 510-518).
Glenn et al., "The Surgical Treatment of Mitral Insufficiency with Particular Reference to the Application of a Vertically Suspended Graft" Jul. 1956 (pp. 59-77).
Glover, et al., "The Fate of Intracardiac Pericardial Grafts as Applied to the Closure of Septal Defects and to the Relief of Mitral Insufficiency" 1952 (pp. 178-185).
Harken et al., "The Surgical Correction of Mitral Insufficienty" Surgical Forum 1954 (pp. 4-7).
Harken et al, "The Surgical Correction of Mitral Insufficiency" The Journal of Thoracic Surgery 1954 (pp. 604-627).
Henderson et al., "The Surgical Treatment of Mitral Insufficiency" Jun. 1953 (pp. 858-868).
International Search and Written Opinion mailed May 11, 2007 filed in corresponding PCT patent application PCT/US06/39011(8 pages).
Johns et al., Mitral Insufficiency: the Experimental Use of a Mobile Polyvinyl sponge Prosthesis: Sep. 1954 (pp. 335-341).
Moore, et al., "Unsuitability of Transventricular Autogenous Slings for Diminishing Valvular Insufficiency" Feb. 1953 (pp. 173-182).
"PVA Datasheet", www.sponge-pva.com/data.htm, Dec. 20, 2006, 2 pages.
"PVA Sponge W (wet) & D (dry)", Ceiba Technologies, http://www.ceibatech.com/PVASpongeW&D.htm, Dec. 20, 2007 5 pages.
Sakakibara, "A Surgical Approach to the Correction of Mitral Insufficiency" Aug. 1955 (pp. 196-203).
SPI-Chem™ Vinylec® (Formvar®) Resins, http://www.2spi.com/catalog/submat/formvar-resins.shtml, Dec. 20, 2006, 5 pages.
Trippel et al, "Reinforced Ivalon Sponge as an Aortic Prosthesis* ", Annals of Surgery, Feb. 1960, vol. 151, No. 2, pp. 216-224.
"Vinylec® Resins", http://www.2spi.com/catalog/submat/vinylec-physical.html, Dec. 20, 2006, 1 page.
Matthews, Anatomy of the Heart, Definitions Cardiology Explained and Presented by Robert Matthews, MD, http://www.rjmatthewsmd.com/Definitions/anatomy_ofthe_heart.htm, printed Jul. 28, 2008, 265 pages.
Mullens, Vascular access, Cardiac Catheterization in Congenital Heart Disease; Pediatric and Adult, 2006, Chapter 4, pp. 115-117, 5 pages, Blackwell Futura, USA.
Mullens, Aortic valve dilation, Cardiac Catheterization in Congenital Heart Disease; Pediatric and Adult, 2006, Chapter 19, pp. 487-489, 5 pages, Blackwell Futura, USA.
Mullens, Foreign body removal, Cardiac Catheterization in Congenital Heart Disease; Pediatric and Adult, 2006, Chapter 12, pp. 350-377, 30 pages, Blackwell Futura, USA.
Mullens, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.
Acar et al., AREVA: Multicenter Randomized Comparison of Low-Dose Versus Standard-Dose Anticoagulation in Patients With Mechanical Prosthetic Heart Valves, Circulation, Nov. 1, 1996, 2107-12, vol. 94, No. 9.
Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.
Babaliaros et al., Emerging Applications for Transseptal Left Heart Catheterization—Old Techniques for New Procedures, Journal of the American College of Cardiology, Jun. 3, 2008, 2116-22, vol. 51, No. 22.
Kuck et al., Best of Structural Heart Disease Abstracts, TCT-124, The American Journal of Cardiology, Oct. 20-25, 2007, 58L.
Rinaldi et al., Best of Structural Heart Disease Abstracts, TCT-123, The American Journal of Cardiology, Oct. 20-25, 2007, 57L.

Siminiak et al., Best of Structural Heart Disease Abstracts, TCT-125, The American Journal of Cardiology, Oct. 20-25, 2007, 58L.

B-Lundqvist et al., Transseptal Left Heart Catheterization: A Review of 278 Studies, Clin. Cardiol., Jan. 1986, 21-26, vol. 9.

Bonow et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.

Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, I-8-I-11.

Bryan et al., Prospective randomized comparison of CarboMedics and St. Jude Medical bileaflet mechanical heart valve prostheses: Ten-year follow-up, The Journal of Thoracic and Cardiovascular Surgery, Mar. 2007, 614-622.e2, vol. 133, No. 3.

Burkhoff et al., A randomized multicenter clinical study to evaluate the safety and efficacy of the TandemHeart percutaneous ventricular assist device versus conventional therapy with intraaortic balloon pumping for treatment of cardiogenic shock, American Heart Journal, Sep. 2006, 469.e1-469.e8, vol. 152, No. 3.

Byrne et al., Percutaneous Mitral Annular Reduction Provides Continued Benefit in an Ovine Model of Dilated Cardiomyopathy, Downloaded from circ.ahajournals.org, Aug. 26, 2008, 3088-92.

Carpentier et al., Reconstructive surgery of mitral valve incompetence Ten-year appraisal, The Journal of Thoracic and Cardiovascular Surgery, Mar. 1980, 338-348, vol. 79, No. 3.

Casselman et al., Mitral Valve Surgery Can Now Routinely Be Performed Endoscopically, Downloaded from circ.ahajournals.org, Aug. 26, 2008, II-48-II-54.

Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.

ClinicalTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091?term=mitral+regurgitation&rank=2, Aug. 25, 2008, 1-3.

ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.

ClinicalTrials.gov, Montreal Safety and Efficacy of the Percutaneous Transvenous Mitral Annuloplasty Device (PTOLEMY), http://clinicaltrials.gov/ct2/show/NCT00571610?term=mitral+regurgitation&rank=13, Aug. 25, 2008, 1-4.

ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.

ClinicalTrials.gov, RESTOR-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.

ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.

ClinicalTrials.gov, VIVID—Valvular and Ventricular Improvement Via iCoapsys Delivery—Feasibility Study, http://clinicaltrials.govict2/show/NCT00512005?term=mitral+valve&rank=12, Aug. 25, 2008, 1-4.

Crabtree et al., Recurrent Mitral Regurgitation and Risk Factors for Early and Late Mortality After Mitral Valve Repair for Functional Ischemic Mitral Regurgitation, The Society of Thoracic Surgeons, 2008, 1537-43, 85.

Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.

De Bonis et al., Similar long-term results of mitral valve repair for anterior compared with posterior leaflet prolapse, The Journal of Thoracic and Cardiovascular Surgery, Feb. 2006, 364-370, vol. 131, No. 2.

Deloche et al., Valve repair with Carpentier techniques the second decade, The Journal of Thoracic and Cardiovascular Surgery, Jun. 1990, 990-1002, vol. 99, No. 6.

De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.

Detaint et al., Surgical Correction of Mitral Regurgitation in the Elderly—Outcomes and Recent Improvements, Downloaded from circ.ahajournals.org, Aug. 26, 2008, 265-272.

Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.

Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.

Epstein et al., Gross and Microscopic Pathological Changes Associated With Nonthoracotomy Implantable Defibrillator Leads, Downloaded from circ.ahajournals.org, Jul. 23, 2008, 1517-24.

Epstein et al, Embolic Complications Associated With Radiofrequency Catheter Ablation, The American Journal of Cardiology, Mar. 15, 1996, 655-658, vol. 77.

Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.

Feldman et al., Patient selection for percutaneous mitral valve repair: insight from early clinical trial applications, Nature Clinical Practice Cardiovascular Medicine, Feb. 2008, 84-90, vol. 5, No. 2.

Feldman et al., Percutaneous Mitral Valve Repair Using the Edge-to-Edge Technique—Six-Month Results of the Everest Phase I Clinical Trial, Journal of the American College of Cardiology, Dec. 6, 2005, 2134-40, vol. 46, No. 11.

Fernandez et al, Early and late-phase events after valve replacement with the St. Jude Medical prosthesis in 1200 patients, The Journal of Thoracic and Cardiovascular Surgery, Feb. 1994, 394-407, vol. 107, No. 2.

Gillinov et al., Durability of Mitral Valve Repair for Degenerative Disease, The Journal of Thoracic and Cardiovascular Surgery, Nov. 1998, 734-743, vol. 116, No. 5.

Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.

Grossi et al., Late Results of Mitral Valve Reconstruction in the Elderly, The Society of Thoracic Surgeons, 2000, 1224-6, 70.

Grossi et al., Minimally Invasive Mitral Valve Surgery: A 6-Year Experience With 714 Patients, The Society of Thoracic Surgeons, 2002, 660-4, 74.

Hendren et al., Mitral Valve Repair for Ischemic Mitral Insufficiency, The Society of Thoracic Surgeons, 1991, 1246-52, 52.

Heupler et al., Infection Prevention Guidelines for Cardiac Catheterization Laboratories, Catheterization and Cardiovascular Diagnosis, 1992, 260-263, 25.

Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.

Ibrahim et al., The St. Jude Medical prosthesis—A thirteen-year experience, The Journal of Thoracic and Cardiovascular Surgery, Aug. 1994, 221-230, vol. 108, No. 2.

Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.

Kasegawa et al., Mitral Valve Repair for Anterior Leaflet Prolapse With Expanded Polytetrafluoroethylene Sutures, The Society of Thoracic Surgeons, 2006, 1625-31, 81.

Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.

International Search Report and Written Opinion dated Sep. 22, 2008 issued in PCT Application No. PCT/US08/63560, 11 pages.

International Search Report and Written Opinion dated Sep. 29, 2008 issued in PCT Application No. PCT/US08/63568, 12 pages.

Kerensky, Complications of Cardiac Catheterization and Strategies to Reduce Risks, Diagnostic and Therapeutic Cardiac Catheterization, 1998, Chapter 8, 91-105.

Koertke et al., INR Self-Management Permits Lower Anticoagulation Levels After Mechanical Heart Valve Replacement, downloaded from circ.ahajournals.org, Aug. 26, 2008, II-75-II-78.

Kratz et al., St. Jude Prosthesis for Aortic and Mitral Valve Replacement: A Ten-Year Experience, The Society of Thoracic Surgeons, 1993, 462-8, 56.

Kron et al., Surgical Relocation of the Posterior Papillary Muscle in Chronic Ischemic Mitral Regurgitation, The Society of Thoracic Surgeons, 2002, 600-1, 74.

Kuwahara et al., Mechanism of Recurrent/Persistent Ischemic/Functional Mitral Regurgitation in the Chronic Phase After Surgical Annuloplasty—Importance of Augmented Posterior Leaflet Tethering, Circulation, Jul. 4, 2006, I-529-I-534.

Laskey et al., Multivariable Model for Prediction of Risk of Significant Complication During Diagnostic Cardiac Catheterization, Catheterization and Cardiovascular Diagnosis, 1993, 185-190, 30.

Lee et al., Mitral Valve Reconstruction: Experience Related to Early and Late Mortality and Reoperation, J Heart Valve Dis, Nov. 2005, 715-721, vol. 14, No. 6.

Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.

Lim et al., Percutaneous Transthoracic Ventricular Puncture for Diagnostic and Interventional Catheterization, Catheterization and Cardiovascular Interventions, 2008, 915-918, 71.

Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.

Lozonschi et al., Transapical Mitral Valved Stent Implantation, The Society of Thoracic Surgeons, 2008, 745-8, 86.

Mack, Percutaneous Therapies for Mitral Regurgitation: Where Do We Stand and Where Are We Going? Do Current Devices Really Represent a Step Forward Compared to Surgery?, 2007 Heart Valve Summit, Jun. 7, 2007, 59 pages.

Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.

Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.

McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.

Mehra et al., Surgery for Severe Mitral Regurgitation and Left Ventricular Failure: What Do We Really Know?, Journal of Cardiac Failure, Mar. 2008, 145-150. vol. 14, No. 2.

Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.

Messas et al., Efficacy of Chordal Cutting to Relieve Chronic Persistent Ischemic Mitral Regurgitation, Circulation, Sep. 9, 2003, II-111-II-115.

Meurin et al., Thromboembolic events early after mitral valve repair: Incidence and predictive factors, International Journal of Cardiology, 2008, 45-52, 126.

Mirable et al., What are the characteristics of patients with severe, symptomatic, mitral regurgitation who are denied surgery?, The European Society of Cardiology, 2007, 1358-65, 28.

Mitchell et al., Complications, Cardiac catheterization and coronary intervention, Chapter 9, 2008, 238-270.

Mishra et al., Coapsys Mitral Annuloplasty for Chronic Functional Ischemic Mitral Regurgitation: 1-Year Results, The Society of Thoracic Surgeons, 2006, 42-46, 81.

Morgan et al., Left Heart Catheterization by Direct Ventricular Puncture: Withstanding the Test of Time, Catheterization and Cardiovascular Diagnosis, 1989, 87-90, 16.

Murday et al., A Prospective Controlled Trial of St. Jude Versus Starr Edwards Aortic and Mitral Valve Prostheses, The Society of Thoracic Surgeons, 2003, 66-74, 76.

Nifong et al., Robotic mitral valve surgery: A United States multicenter trial, The Journal of Thoracic and Cardiovascular Surgery, Jun. 2005, 1395-1404, vol. 129, No. 6.

Noto et al., Cardiac Catheterization 1990: A Report of the Registry of the Society for Cardiac Angiography and Interventions (SCA&I), Catheterization and Cardiovascular Diagnosis, 1991, 75-83, 24.

Ohlow et al., Incidence and outcome of femoral vascular complications among 18,165 patients undergoing cardiac catheterisation, International Journal of Cardiology, 2008, 1-6.

Piazza et al., Transcatheter Mitral Valve Repair for Functional Mitral Regurgitation: Coronary Sinus Approach, Journal of Interventional Cardiology, 2007, 495-508, vol. 20, No. 6.

Pedersen et al., iCoapsys Mitral Valve Repair System: Percutaneous Implantation in an Animal Model, Catheterization and Cardiovascular Interventions, 2008, 125-131, 72.

Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.

Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.

Ruiz, New Percutaneous Approaches for Mitral Regurgitation, Lenox Hill Heart and Vascular Institute of New York, May 13-16, 2008, 26 pages.

Rumel et al., Section on Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.

Seeburger et al., Minimal invasive mitral valve repair for mitral regurgitation: results of 1339 consecutive patients, European Journal of Cardio-thoracic Surgery, 2008, 1-6.

Southard et al., Current Catheter-Based Treatments of Functional Mitral Regurgitation, Cardiac Interventions Today, Jun. 2007, 41-44.

Svensson et al., United States Feasibility Study of Transcatheter Insertion of a Stented Aortic Valve by the Left Ventricular Apex, The Society of Thoracic Surgeons, 2008, 46-55, 86.

Toledano et al., Mitral regurgitation: Determinants for referral for cardiac surgery by Canadian cardiologists, Can J. Cardiol, Mar. 1, 2007, 209-214, vol. 23, No. 3.

Tops et al., Percutaneous Valve Procedures: An Update, Curr Probl Cardiol, Aug. 2008, 417-426.

Walther et al., Transapical minimally invasive aortic valve implantation; the initial 50 patients, European Journal of Cardio-thoracic Surgery, 2008, 983-988, 33.

Webb et al., Percutaneous Mitral Annuloplasty With the MONARC System: Preliminary Results From the EVOLUTION Trial, TCT-103, The American Journal of Cardiology, Oct. 22-27, 2006, 49M.

Webb et al., Percutaneous Transvenous Mitral Annuloplasty—Initial Human Experience with Device Implantation in the Coronary Sinus, downloaded from circ.ahajournals.org, Aug. 26, 2008, 851-855.

Webster et al., Impact of transvenous ventricular pacing leads on tricuspid regurgitation in pediatric and congenital heart disease patients, J Interv Card Electrophysiol, 2008, 65-68, 21.

Ye et al., Six-month outcome of transapical transcatheter aortic valve implantation in the initial seven patients, European Journal of Cardiothoracic Surgery, 2007, 16-21, 31.
Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.
Zhou et al., Thromboembolic Complications of Cardiac Radiofrequency Catheter Ablation: A Review of the Reported Incidence, Pathogenesis and Current Research Directions, Journal of Cardiovascular Electrophysiology, Apr. 1999, 611-620, vol. 10, No. 4.
Eisenhauer et al., Closure of Prosthetic Paravalvular Mitral Regurgitation With the Gianturco-Grifka Vascular Occlusion Device, Catheterization and Cardiovascular Interventions, 2001, 5 pages,vol. 54.
Hourihan et al., Transcatheter Umbrella Closure of Valvular and Paravalvular Leaks, American College of Cardiology, Nov. 15, 1992, 7 pages, vol. 20, No. 6.
Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.
Rashkind et al. Nonsurgical closure of patent ductus arteriosus: clinical application of the Rashkind PDA Occluder System, Therapy and Prevention—Congenital Heart Disease, Mar. 1987, 10 pages, vol. 75, No. 3.
Ryhänen et al., Invivo biocompatibility evaluation of nickel-titanium shape memory metal alloy: Muscle and perineural tissue responses and encapsule membrane thickness, Muscle and Perineural Tissue Response to Nitinol, Received Aug. 11, 1997; accepted Jan. 19, 1998, 8 pages.
International Search Report and Written Opinion dated Jan. 16 2009 issued in PCT Application No. PCT/US08/83497, 10 pages.
Balzer et al., Real-time transesophageal three-dimensional echocardiography for guidance of percutaneous cardiac interventions: first experience, Clinical Research in Cardiology, May 29, 2008, 565-574, vol. 97, No. 9.
Carlson et al., Lead Perforation: Incidence in Registries, Pace Industry Viewpoint, Jan. 2008, 13-15, vol. 31.
Clinical Trials.gov, Comparing the Effectiveness of a Mitral Valve Repair Procedure in Combination With Coronary Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.
Clinical Trials.gov, Safety and Efficacy Study of the PTMA Device to Reduce Mitral Valve Regurgitation in Patients With Heart Failure (PTOLEMY2Canada), http://clinicaltrials.gov/ct2/show/study/NCT00815386?term=Viacor&rank=3, Verified by Viacor Dec. 2008, Downloaded from internet Feb. 24, 2009, 1-3.
Clinical Trials.gov, Study of Safety and Efficacy of the Percutaneous Reduction of Mitral Valve Regurgitation in Heart Failure Patients (PTOLEMY-2), http://clinicaltrials.gov/ct2/show/NCT00787293?term=Viacor&rank=5, Verified by Viacor Nov. 2008, Downloaded from internet Feb. 24, 2009, 1-2.
Cohen, Trans-Septal Technique for Tandemheart Insertion, Lenox Hill Heart and Vascular Institute of New York, Barcelona May 22-May 25, 2007, 18 pages.
Corbisiero et al., Does Size Really Matter? A Comparison of the Riata Lead Family Based on Size and Its Relation to Performance, Pace, Jun. 2008, vol. 31, 722-726.
Criber et al., Treatment of Calcific Aortic Stenosis With the Percutaneous Heart Valve—Mid-Term Follow-Up From the Initial Feasibility Studies: The French Experience, Journal of the American College of Cardiology, Mar. 21, 2006, vol. 47, No. 6, 1241-1223.
Danik et al., Timing of delayed perforation with the St. Jude Riata lead: A single-center experience and a review of the literature, Heart Rhythm Society, Dec. 2008, vol. 5, No. 12, 1667-1672.
Del Valle-Fernández et al., Transcatheter heart valves for the treatment of aortic stenosis: state-of-the-art, Minerva Cardioangiologica, Oct. 2008, vol. 56, No. 5, 543-556.
Douthitt, Cardiac Dimensions® Inc. Receives CE Mark for Carillon™ Mitral Contour System™, Cardiac Dimensions—News, htpp://www.cardiacdimensions.com/usa/press-release-2-4-09.html, downloaded Feb. 24, 2009, 1-2.
Dvorin, Endovalve Inc., Pioneering percutaneous mitral valve replacement., Start-Up Windhover's Review of Emerging Medical Ventures, Jun./Jul. 2006, vol. 11, No. 7, 1-2.
Eltchaninoff, Clinical results of percutaneous aortic valve implantation, Euro PCR07, Cribier-Edwards, May 25, 2007, 30 pages.
Evalve reports 1st MitraClip treatments in the Netherlands, Medical Device Daily, Feb. 19, 2009, vol. 13, No. 32, 2 pages.
A first for MiCardia's Dynoplasty, Medical Device Daily, Feb. 19, 2009, vol. 13, No. 32, 1 page.
Fitts et al., Fluoroscopy-Guided Femoral Artery Puncture Reduces the Risk of PCI-Related Vascular Complications, Journal of Interventional Cardiology, vol. 21, No. 3, 2008, 273-278.
Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132, 2009, 419-428.
Geyfman et al., Cardiac Tamponade as Complication of Active-Fixation Atrial Lead Perforations: Proposed Mechanism and Management Algorithm, PACE, Apr. 2007, vol. 30, 498-501.
Gorman et al., Surgical Therapy for Mitral Regurgitation: The Key to Preventing Heart Failure?, Prevention of Heart Failure After Myocardial Infarction, 2008, 211-215.
Harper, Evalve Announces Enrollment Completion of the Everest Randomized Study, http://www.evalveinc.com/europe/press/17.html, downloaded Feb. 24, 2009, 1-3.
Harper, Two-Year Follow-Up Data Demonstrates Preservation of Adequate Mitral Valve Area in Patients Treated with the MitraClip®-system, http://www.evalveinc.com/europe/press/21.html, downloaded Feb. 24, 2009, 1-3.
Hung et al., 3D Echocardiography: A Review of the Current Status and Future Directions, ASE Position Paper, Journal of the American Society of Echocardiography, Mar. 2007, 213-233.
Hung et al., Mechanism of Dynamic Regurgitant Orifice Area Variation of Functional Mitral Regurgitation—Physiologic Insights From the Proximal Flow Convergence Technique, Journal of the American College of Cardiology, Feb. 1999, vol. 33, No. 2, 538-545.
Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.
Hytowitz, First U.S. Patients Enrolled in the Realism Continued Access Study, evalve, http://www.evalveinc.com/europe/press/22/html, downloaded Feb. 24, 2009, 2 pages.
International Search Report and Written Opinion dated Feb. 25, 2009 issued in PCT Application No. PCT/US08/83570, 13 pages.
International Search Report and Written Opinion dated Apr. 2, 2009 issued in PCT Application No. PCT/US08/83574, 8 pages.
Jilaihawi et al., Percutaneous Aortic Valve Replacement in Patients with Challenging Aortoiliofemoral Access, Catheterization and Cardiovascular Interventions, 2008, vol. 72, 885-890.
Jovin et al., Atrial Fibrillation and Mitral Valve Repair, Pace, Aug. 2008, vol. 31, 1057-1063.
Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journal of the American Society of Echocardiography, Aug. 2008, vol. 21, No. 8, 912-921.
Kempfert et al., Minimally invasive off-pump valve-in-a-valve implantation: the atrial transcatheter approach for reoperative mitral valve replacement, European Heart Journal, 2008, vol. 29, 2382-2387.
Kerensky, Complications of Cardiac Catheterization and Strategies to Reduce Risks, Diagnostic and Therapeutic Cardiac Catheterization—Third Edition—Chapter 8, 1998, 17 pages.
Kodali et al., Transcatheter Valve Repair and Replacement, Downloaded from arjournals.annualreviews.org by National Institute of Health Library on Feb. 25, 2009, 14 pages.

Kwan et al., Geometric Differences of the Mitral Apparatus Between Ischemic and Dilated Cardiomyopathy With Significant Mitral Regurgitation—Real-Time Three-Dimensional Echocardiography Study, Circulation, Mar. 4, 2003, 1135-1140.

Leung et al, Percutaneous Mitral Valve Repair—An overview of the current devices and techniques, Coronory/Cardiac Interventions—Endovascular Today, Oct. 2006, 26-33.

Levine et al., Mechanistic Insights into Functional Mitral Regurgitation, Valvular Heart Disease, 2009, 125-129.

Little et al., Three-Dimensional Ultrasound Imaging Model of Mitral Valve Regurgitation: Design and Evaluation, Ultrasound in Medicine and Biology, 2008, vol. 34, No. 4, 647-654.

Llaneras et al., Large Animal Model of Ischemic Mitral Regurgitation, The Society of Thoracic Surgeons—Ischemic Mitral Insufficiency, 1994, vol. 57, 432-439.

Magne et al., Ischemic Mitral Regurgitation: A Complex Multifaceted Disease, Cardiology, 2009, vol. 112, 244-259.

McClure et al., Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.

Modi et al., Minimally invasive mitral valve surgery: a systematic review and meta-analysis, European Journal of Cardio-Thoracic Surgery, 2008, vol. 34, 943-952.

Y, Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.

Ning et al., Live three-dimensional transesophageal echocardiography in mitral valve surgery, Chinese Medical Journal, 2008, vol. 121, No. 20, 2037-2041.

Nötzold et al., Microemboli in aortic valve replacement, Future Drugs Ltd, Expert Rev. Cardiovasc. Ther., vol. 4, No. 6, 2006, 853-859.

Onundarson et al., Warfarin anticoagulation intensity in specialist-based and in computer-assisted dosing practice, International Journal of Laboratory Hematology, 2008, vol. 30, 382-389.

Otsuji et al., Insights From Three-Dimensional Echocardiography Into the Mechanism of Functional Mitral Regurgitation—Direct in Vivo Demonstration of Altered Leaflet Tethering Geometry, Circulation, Sep. 16, 1997, vol. 96, No. 6, 1999-2008.

Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.

Pai et al., Effect of Atrial Fibrillation on the Dynamics of Mitral Annular Area, J. Heart Valve Dis., Jan. 2003, vol. 12, No. 1, 31-37.

Palacios et al., Safety and Feasibility of Acute Percutaneous Septal Sinus Shortening: First-In-Human Experience, Catheterization and Cardiovascular Interventions, 2007, vol. 69, 513-518.

Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.

Rodés-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.

Satpathy et al., Delayed Defibrillator Lead Perforation: An Increasing Phenomenon, Pace, Jan. 2008, vol. 31, 10-12.

Schofer, Percutaneous MVR: Clinical Evaluation—The Carillon Experience, EuroPCR 2007, Barcelona, Spain, May 22-25, 2007, 35 pages.

Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.

Spencer, Viacor, Inc. Announces First Patient Treated in PTOLEMY-2 Study, http://www.viacorinc.com/viacor_news.html, Nov. 14, 2008, downloaded Feb. 24, 2009, 2 pages.

Sterliński et al., Subacute cardiac perforations associated with active fixation leads, Clinical Research Leads and Lead Extraction, Europace, 2009, vol. 11, 206-212.

Turakhia et al., Rates and severity of perforation from implantable cardioverter-defibrillator leads: A 4-year study, J Interv Card Electrophysiol, 2009, vol. 24, 47-52.

Vahanian, The Cardiologist's Perspective on the Future of Percutaneous Mitral Valve Repair, Euro PCR07, May 22-25, 2007, 53 pages.

Vahanian, Coronary Sinus and Direct Annuloplasty Percutaneous Mitral Valve Repair, Innovations in Cardiovascular Interventions, Dec. 7-9, 2008, Tel-Aviv, Israel, 45 pages.

Vahanian, Overview on Percutaneous Mitral Valve Technology, Euro PCR07, Transcatheter Valve Symposium, Barcelona, May 22-25, 2007, 29 pages.

Van Gelder et al., Diagnosis and Management of Indavertently Placed Pacing and ICD Leads in the Left Ventricle: A Multicenter Experience and Review of the Literature, Pace, May 2000, vol. 23, 877-883.

Vranckx et al., The TandemHeart®, percutaneous transseptal left ventricular assist device: a safeguard in high-risk percutaneous coronary interventions. The six-year Rotterdam experience, Clinical research EuroInterv., 2008, vol. 4, 331-337.

Wolf et al., Solid and gaseous cerebral micorembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.

Xiangming et al., In Vivo Characterization of Attachment Safety Between Cardiac Pacing Lead and Canine Heart Muscle*, Acta Mechanica Solida Sinica, Sep. 2007, vol. 20, No. 3, 189-197.

Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.

Yosefy et al., Proximal Flow Convergence Region as Assessed by Real-time 3-Dimensional Echocardiography: Challenging the Hemispheric Assumption, Journal of the American Society of Echocardiography, Apr. 2007, Vol., No. 4, 389-396.

U.S. Office Action dated Jul. 8, 2009 issued in U.S. Appl. No. 11/258,828, 7 pages.

International Search Report and Written Opinion dated Aug. 11, 2009 issued in PCT Application No. PCT/US2009/046995, 11 pages.

U.S. Office Action dated Sep. 29, 2009 issued in U.S. Appl. No. 12/209,686, 9 pages.

U.S. Office Action dated Dec. 15, 2009 issued in U.S. Appl. No. 11/258,828, 12 pages.

U.S. Office Action dated Jan. 8, 2010 issued in U.S. Appl. No. 11/748,147, 63 pages.

U.S. Office Action dated Jan. 14, 2010 issued in U.S. Appl. No. 11/940,674, 59 pages.

U.S. Office Action dated Jan. 25, 2010 issued in U.S. Appl. No. 11/748,121, 9 pages.

U.S. Office Action dated Feb. 4, 2010 issued in U.S. Appl. No. 11/748,138, 58 pages.

U.S. Office Action dated Jun. 2, 2010 issued in U.S. Appl. No. 12/209,686, 15 pages.

U.S. Office Action dated Jun. 28, 2010 issued in U.S. Appl. No. 11/258,828, 14 pages.

Notice of Allowance dated Jul. 1, 2010 issued in U.S. Appl. No. 11/940,674, 6 pages.

International Search Report and Written Opinion dated Jul. 6, 2010 issued in PCT Patent Application No. PCT/US2010/032764, 9 pages.

U.S. Office Action dated Jul. 20, 2010 issued in U.S. Appl. No. 11/748,147, 15 pages.

Ryhänen et al., In vivo biocompatibility evaluation of nickel-titanium shape memory metal alloy: Muscle and perineural tissue responses and encapsule membrane thickness, Muscle and Perineural Tissue Response to Nitinol, Jan. 19, 1998, pp. 481-488.

U.S. Office Action dated Aug. 30, 2010 issued in U.S. Appl. No. 11/748,138, 9 pages.

U.S. Office Action dated Aug. 31, 2010 issued in U.S. Appl. No. 11/748,121, 11 pages.

International Search Report and Written Opinion dated Sep. 21, 2010 issued in PCT Patent Application No. PCT/US2010/043360, 9 pages.

Extended European search report dated Nov. 30, 2010 issued in European Patent Application No. 08850467.5, 6 pages.

Extended European search report dated Nov. 30, 2010 issued in European Patent Application No. 08755418.4, 7 pages.
Extended European search report dated Nov. 30, 2010 issued in European Patent Application No. 08849442.2, 6 pages.
Extended European Search Report dated Dec. 1, 2010 issued in European Patent Application No. 08755426.7, 6 pages.
Extended European Search Report dated Dec. 14, 2010 issued in European Patent Application No. 06816336.9, 7 pages.
U.S. Office Action dated Mar. 21, 2011 issued in U.S. Appl. No. 11/258,828, 22 pages.
U.S. Office Action dated Mar. 29, 2011 issued in U.S. Appl. No. 11/748,121, 14 pages.
U.S. Office Action dated Apr. 4, 2011 issued in U.S. Appl. No. 11/940,724, 65 pages.
European Examination Report dated Aug. 4, 2011 issued in European Patent No. 06 816 336.9, 3 pages.
U.S. Office Action dated Aug. 29, 2011 issued in U.S. Appl. No. 111940,694, 11 pages.
European Examination Report dated Aug. 11, 2011 issued in European Patent No. 08 755 418.4, 3 pages.
Notice of Allowance dated Oct. 31, 2011 issued in U.S. Appl. No. 11/258,828, 10 pages.
Preliminary Report on Patentability dated Nov. 1, 2011 issued in PCT Patent Application No. PCT/US2010/032764, 4 pages.
U.S. Office Action dated Nov. 3, 2011 issued in U.S. Appl. No. 12/872,228, 8 pages.
Notice of Allowance dated Dec. 14, 2011 issued in U.S. Appl. No. 12/431,399, 12 pages.
U.S. Office Action dated Dec. 21, 2011, issued in U.S. Appl. No. 11/748,121, 9 pages.
U.S. Office Action dated Jan. 18, 2012 issued in U.S. Appl. No. 11/940,724, 10 pages.
International Preliminary Report on Patentability dated Jan. 31, 2012 issued in PCT Patent Application No. PCT/US2010/043360, 7 pages.
U.S. Office Action dated Feb. 15, 2012 issued in U.S. Appl. No. 11/940,694, 9 pages.
U.S. Notice of Allowance dated Mar. 8, 2012 issued in U.S. Appl. No. 12/872,228, 7 pages.
U.S. Office Action dated Jun. 20, 2012 issued in U.S. Appl. No. 11/940,694, 9 pages.
U.S. Office Action dated Jun. 21, 2012 issued in U.S. Appl. No. 11/748,147, 29 pages.
Notice of Allowance dated Jul. 20, 2012 issued in U.S. Appl. No. 11/748,121, 10 pages.
U.S. Office Action dated Sep. 19, 2012, issued in U.S. Appl. No. 12/510,929, 10 pages.
U.S. Office Action dated Oct. 9, 2012, issued in U.S. Appl. No. 12/872,228, 7 pages.
U.S. Notice of Allowance dated Nov. 21, 2012, issued in U.S. Appl. No. 11/748,121, 8 pages.
European Intent to Grant dated Feb. 22, 2013 issued in European Patent Application No. 08 755 418.4, 7 pages.
European Search Report dated Mar. 6, 2013 issued in European Patent Application No. 10804952.9, 8 pages.
Notice of Allowance dated Mar. 8, 2013 issued in U.S. Appl. No. 11/748,138, 9 pages.
Final Office Action dated Mar. 13, 2013 issued in U.S. Appl. No. 11/748,147, 10 pages.
Final Office Action dated Mar. 22, 2013 issued in U.S. Appl. No. 12/510,929, 13 pages.
Notice of Allowance dated Jun. 3, 2013 issued in U.S. Appl. No. 12/872,228, 7 pages.

* cited by examiner

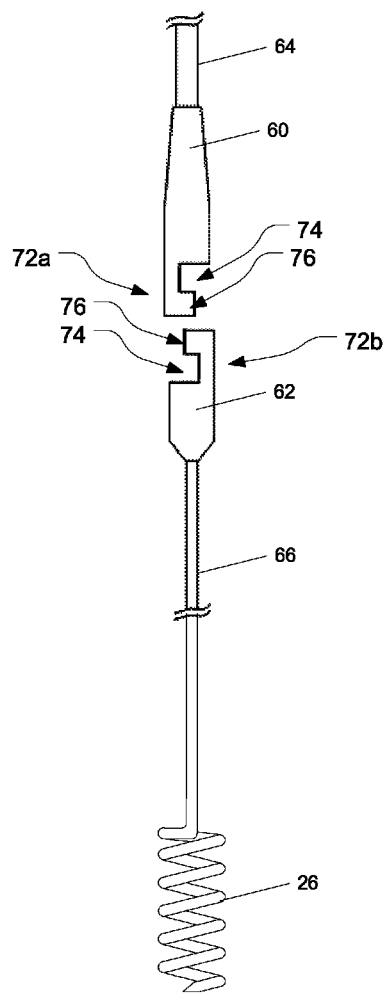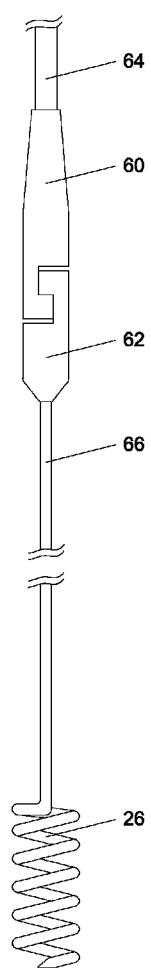

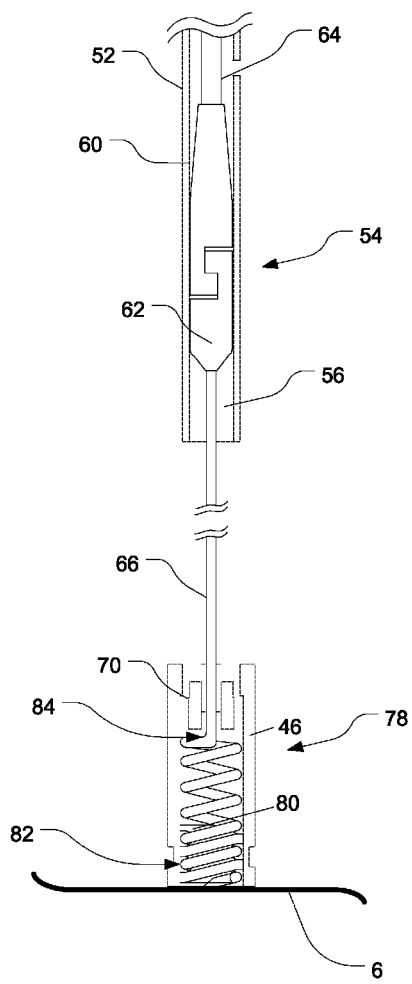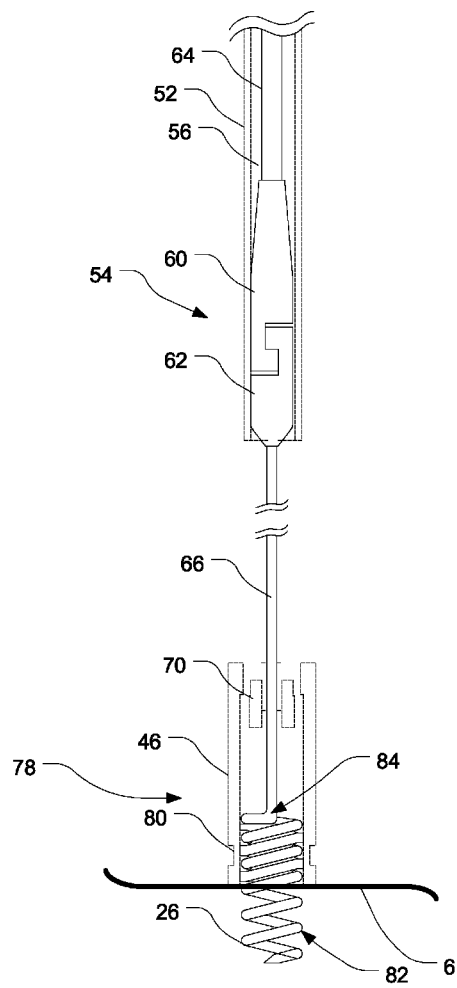

IMPLANT DELIVERY AND DEPLOYMENT SYSTEM AND METHOD

CROSS REFERENCE TO RELATED APPLICATIONS

The subject application is a continuation of U.S. patent application Ser. No. 12/431,399, now U.S. Pat. No. 8,216,302, filed Apr. 28, 2012 which is a continuation-in-part of U.S. patent application Ser. No. 11/258,828, now U.S. Pat. No. 8,092,525 filed on Oct. 26, 2005, U.S. patent application Ser. No.: 11/940,694, filed Nov. 15, 2007, and U.S. patent application Ser. No. 12/209,686, filed Sep. 12, 2008, the entire disclosures of which are incorporated herein by reference

FIELD

The present disclosure relates to the repair and/or correction of dysfunctional heart valves, and more particularly pertains to heart valve implants and systems and methods for delivery and implementation of the same.

BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement is carried out as an open heart procedure. The repair or replacement surgery may last in the range of about three to five hours, and is carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

BRIEF DESCRIPTION OF THE DRAWINGS

Features and advantage of the claimed subject matter will be apparent from the following description of embodiments consistent therewith, which description should be considered in conjunction with the accompanying drawings, wherein:

FIG. 5 depicts one embodiment of a latching mechanism comprising a first and second latching pin in a decoupled position consistent with the present disclosure;

FIG. 6 depicts one embodiment of a latching mechanism comprising a first and second latching pin in a coupled position consistent with the present disclosure;

FIG. 7 depicts a partial view of one embodiment of an implant and latching mechanism with the anchoring mechanism in a retracted position consistent with the present disclosure;

FIG. 8 depicts a partial view of one embodiment of an implant and latching mechanism with the anchoring mechanism in an extended position consistent with the present disclosure;

DESCRIPTION

Figure 1:
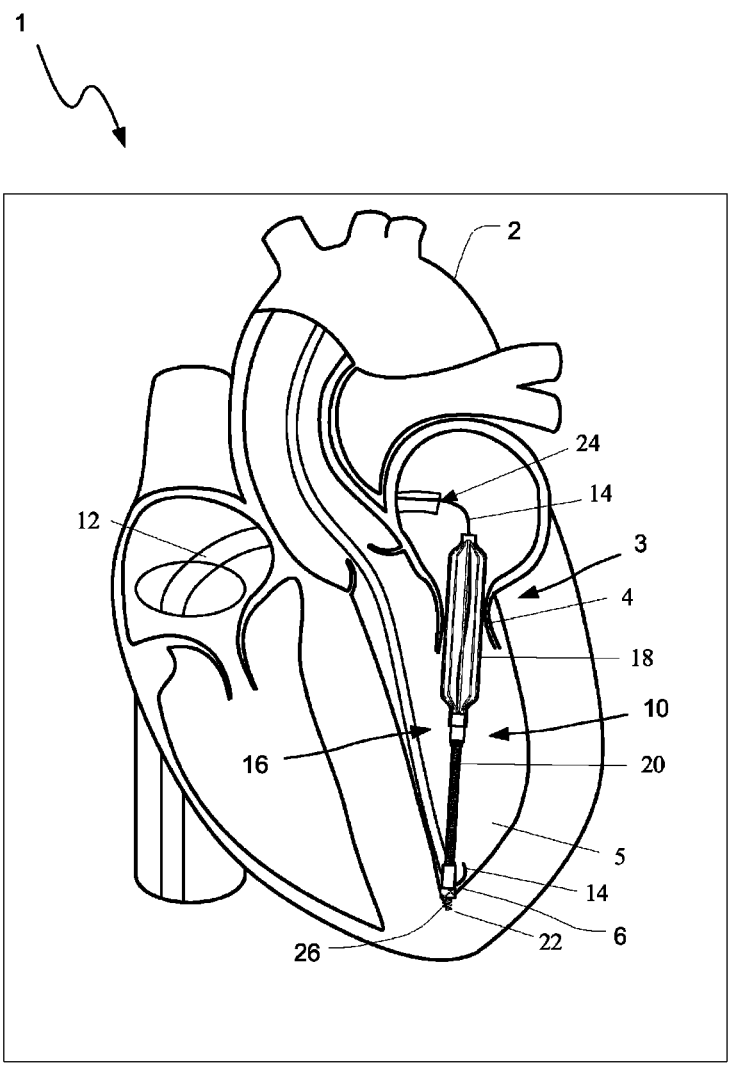
FIG. 1 is a perspective view of one embodiment of a mitral valve implant delivery system consistent with the present disclosure.

Referring to FIG. 1, a perspective view of one embodiment of a percutaneous delivery system 1 for delivering and/or recapturing a mitral valve implant 10 within the heart is shown. The delivery system 1 may include a mitral valve implant 10, a delivery catheter 12, a guidewire 14 and a deployment/clamping mechanism 16 configured to releasably couple the implant 10 to a delivery wire (not shown). The implant 10 may comprise a spacer 18, a shaft or stop tube 20 and an anchoring mechanism 22. In general, the mitral valve implant 10 may be delivered within the heart 1 and anchored to the native coronary tissue 6 as generally illustrated in FIG. 1 such that at least a portion of the spacer 18 is disposed proximate a mitral valve 3 and the mitral valve implant 10 may interact and/or cooperate with at least a portion of the native mitral valve 3 to reduce and/or eliminate excessive regurgitation, for example, as discussed in U.S. patent application Ser. No. 12/209,686, filed on Sep. 12, 2008 and entitled SYSTEM AND METHOD FOR IMPLANTING A HEART IMPLANT, the entire disclosure of which is incorporated herein by reference. For example, at least a portion of one or more cusps 4 of the heart 1 valve may interact with, engage, and/or seal against at least a portion of the heart valve implant 10 (for example, but not limited to, the spacer 18) when the heart valve 3 is in a closed condition. The interaction, engagement and/or sealing between at least a portion of at least one cusp 4 and at least a portion of the heart valve implant 10 may reduce and/or eliminate regurgitation in a heart valve 3, for example, providing insufficient sealing, including only a single cusp 4, e.g., following removal of a diseased and/or damaged cusp 4, and/or having a ruptured cordae. A heart valve implant 10 consistent with the present disclosure may be used in connection with various additional and/or alternative defects and/or deficiencies.

As shown, the delivery system 1 may include a delivery catheter 12 (for example, but not limited to, a steerable delivery catheter) configured to be percutaneously introduced or inserted into one or more vessels of the body (e.g., one or more veins and/or arteries) and conveyed to the heart 1 for delivery and/or recapture of the mitral valve implant 10. Conveyance of the catheter 12 and/or of the mitral valve implant 10 to the heart 1 may be directed and/or assisted by monitoring the travel of the catheter 12, e.g., via radiographic and/or other imaging techniques and/or by passing the catheter 12 through another, larger catheter already in place (not shown). The catheter 12 may have a length and outer diameter configured to extend from the incision site in the patient's body through one or more veins and/or arteries to the desired location within the heart 1 (e.g., the left ventricle 5).

The catheter 12 may define at least one lumen 24 having an internal diameter configured to receive and convey the guidewire 14, the deployment mechanism 16 and the implant 10 from a proximal end of the catheter 12 to a distal end of the catheter 12. The catheter 12 may include a flexible material having sufficient rigidity, strength and inner lubricity to be guided through the blood vessels to the heart and to convey the implant 10. For example, the catheter 12 may include a combination or combinations of polymeric and/or metallic materials having an inner diameter of between 5 French size and 50 French size, an outer diameter of between 0.004 inches 0.250 inches larger than the corresponding inner diameter, and a length of between 10 centimeters and 200 centimeters.

The guidewire 14 may be configured to be disposed within the lumen 24 of the catheter 12 and may have a length greater than the length of the catheter 12. The guidewire 14 may include a flexible wire having sufficient strength and/or rigidity to convey and/or urge the implant 10 through the lumen 24 of the catheter 12. For example, the guidewire 14 may include a combination or combinations of polymeric and/or metallic materials having a diameter of between 0.004 inches and 0.060 inches and a length of between 100 centimeters and 500 centimeters. Consistent with at least one embodiment herein, the guidewire 14 may have a diameter of ⅟₃₂".

Figure 2:
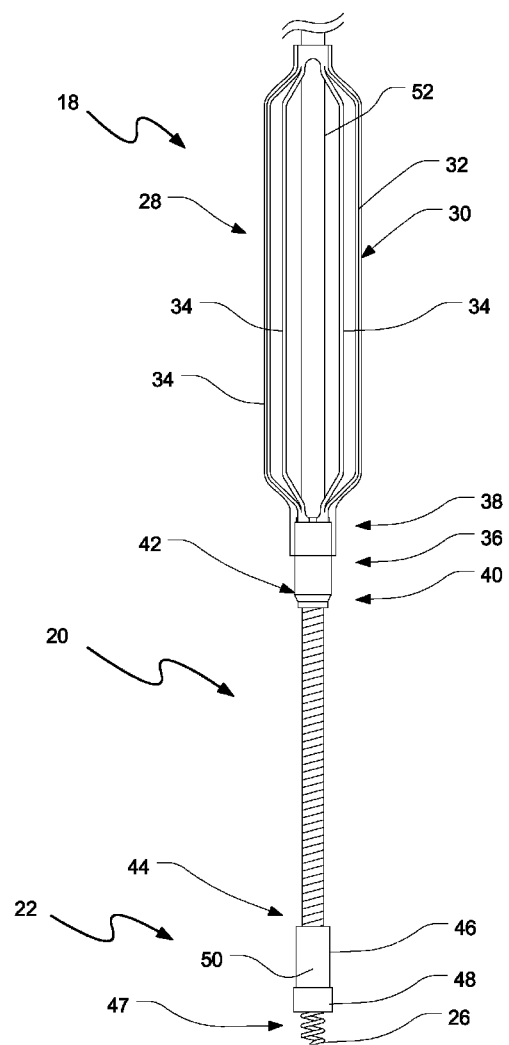
FIG. 2 depicts a plan view of one embodiment of an implant consistent with the present disclosure.

Turning now to FIG. 2, an implant 10 consistent with at least one embodiment of herein is illustrated. The implant 10 may comprise a spacer or valve body portion 18 (for example, a resiliently deformable spacer configured to be received in the lumen 24 of the catheter 12) which may be coupled to a shaft 20. The shaft 20 may be coupled to at least one anchor portion/mechanism 22 configured to couple, attach, and/or otherwise secure the mitral valve implant 10 to native coronary tissue 6. According to one embodiment, at least a portion of the anchor mechanism 22 may include a generally helical screw or the like 26 configured to be at least partially screwed into the native coronary tissue 6.

The spacer 18 may comprise a spacer cage 28 having at least a portion of the outer surface 30 covered with a balloon 32. The spacer cage 28 and/or the balloon 32 may comprise a resiliently flexible structure configured to at least partially collapse from an expanded position as illustrated to a retracted or collapsed position. When in the collapsed position, the spacer cage 28 and balloon 32 may be configured to be received in and advanced along the lumen 24 of the delivery catheter 12. When in the expanded position, the spacer cage 28 and balloon 32 may be configured to interact and/or cooperate with at least a portion of the native mitral valve 3 (e.g., at least one cusp 4) to reduce and/or eliminate excessive regurgitation as generally illustrated in FIG. 1.

The spacer cage 28 may comprise a frame or ribbed structure, for example, a frame of resilient flexible material such as, but not limited to, shape memory materials (for example, but not limited to, nickel titanium compositions (e.g., Nitinol) or the like). The spacer cage 28 may comprise a plurality of support structures or ribs 34 extending generally along the longitudinal axis of the implant 10. The support structures 34 may be configured to resiliently bend radially inwardly and/or outwardly, for example, to facilitate loading of the implant 10 within the delivery catheter 12 and/or to facilitate sealing with the mitral valve 3. The number and location of the support structures 34 may depend upon the particulars of the patient's condition as well as the desired flexibility and desired shape of the spacer 18. For example, the implant 10 may comprise between 5 to 12 support structures 34.

The balloon 32 may be configured to be at least partially disposed about the outer surface 30 of the spacer cage 28. The balloon 32 may comprise a resilient flexible, biologically acceptable material. For example, the balloon 32 may comprise Elasteon™ material or the like configured to generally encapsulate the outer surface 30 of the spacer cage. The balloon 32 may be coupled or otherwise secured to at least a portion of one or more of the support structures 34 (for example, but not limited to, overmolding, adhesives, and/or laminating) and/or may be only secured about the ends of the spacer cage 28.

The spacer 18 may therefore be configured to interact and/or cooperate with at least a portion of the native mitral valve 3 to reduce and/or eliminate excessive regurgitation. As such, the configuration and/or geometries of the spacer 18 may depend upon the particulars of the condition of the patient's mitral valve 3 and the damage thereto. The implant 10 may have sufficient overall flexibility to facilitate advancement of the implant 10 within the delivery catheter 12 to minimize the potential of the implant 10 becoming wedged or stuck within the delivery catheter 12. In addition, the implant 10 may also have sufficient overall rigidity to maintain the spacer 18 within the mitral valve 3 such that the implant 10 performs as intended.

The spacer 18 may optionally include a garage 36 configured to couple the spacer 18 to the shaft or stop tube 20. Consistent with at least one embodiment herein, the support structures 34 of the spacer cage 28 may be coupled to the garage 36, for example, about a first end region 38 of the garage 36. A proximal end region 40 of the stop tube 20 may be coupled to a second end region 42 of the garage 36 generally opposite the first end region 38. The distal end region 44 of the stop tube 20 may be coupled to a can 46 configured to receive at least a portion of an anchoring device 47, for example, the helical screw 26. A portion of the can 46 (for example, but not limited to, the distal end region) may include a sheath or pledget 48 configured to stimulate ingrowth of the native coronary tissue 6 over time and to further anchor or secure the implant 10 to the tissue. The garage 36 may also define a cavity 50 configured to engage with the deployment mechanism 16 as described herein.

Figure 3:
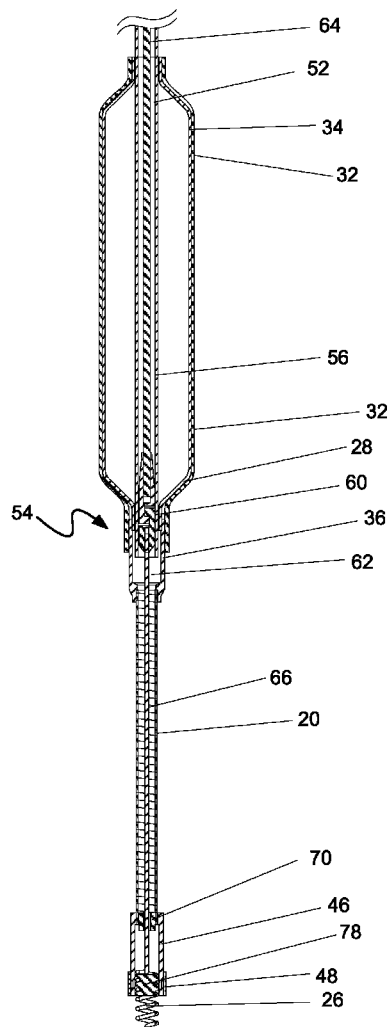
FIG. 3 depicts a cross-sectional view of one embodiment of an implant illustrated in FIG. 2 consistent with the present disclosure.
Figure 4:
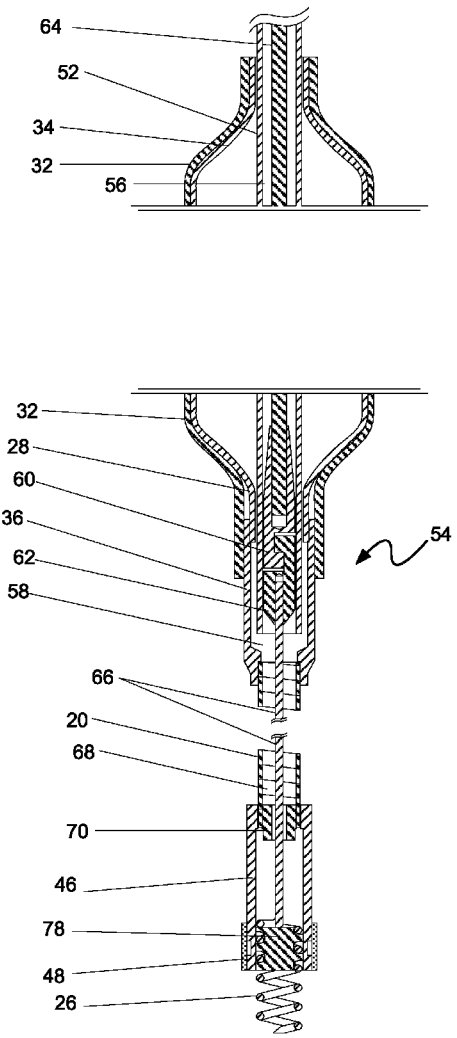
FIG. 4 depicts an explode, cross-sectional view of the implant illustrated in FIG. 3 consistent with the present disclosure.

Turning now to FIGS. 3 and 4, a cross-sectional view of an implant 10 is generally illustrated including a deployment mechanism 16. As will be explained in greater detail herein, the deployment mechanism 16 is configured to be releasably coupled to the implant 10 such that the implant 10 may be advanced through the delivery catheter 12 and secured to the native coronary tissue 6 of the patient's heart 1 (for example, the wall of the left ventricle 5 proximate the apex). According to at least one embodiment, the deployment mechanism 16 may be configured to advance the implant 10 through the delivery catheter 12 to the implant site, rotate the implant 10 to secure the anchoring mechanism 22 to the tissue, and release the implant 10.

The deployment mechanism 16 may comprise a sleeve 52 configured to releasably engage a latching mechanism 54. The sleeve 52 may comprise a generally flexible tubing such as, but not limited to, a poly(tetrafluoroethylene) (PTFE) tube defining an lumen or passageway 56. The sleeve 52 may be configured to be disposed within the lumen 24 of the delivery catheter 12 and extend from within the implant 10 (for example, but not limited to, from the spacer 18 and/or the garage 36) and out beyond the proximal end of the delivery catheter 12. The sleeve 52 may also have an outer surface having a size and/or shape configured to be received within the chamber or cavity 58 of the garage 36. For example, the sleeve 52 may have an outer configuration configured to engage the garage cavity 58 and to provide rotational and/or lateral stability of the sleeve 52 and/or the latching mechanism 54 as is discussed further herein. According to at least one embodiment consistent herein, the sleeve 52 and the cavity 58 of the garage 36 may have a generally cylindrical configuration; however, the sleeve 52 and/or the cavity 58 may have other shapes configured to provide rotational and/or lateral stability of the sleeve 52 and/or the latching mechanism 54. For example, the sleeve 52 and/or the cavity 58 may have a non-circular cross-section such as, but not limited to, a rectangular, triangular or hexagonal shape or the like.

The latching mechanism 54 may comprise a first latch pin 60 configured to cooperate with a second latch pin 62 to form a releasable connection. The first latch pin 60 may be coupled to a delivery wire 64 configured to be received within the lumen 56 of the sleeve 52 and to extend beyond the distal end of the sleeve 52.

The second latch pin 62 may be coupled to a portion of the implant 10 such as, but not limited to, the spacer 18, stop tube 20, and/or the anchoring mechanism 22. For example, the second latch pin 62 may be coupled to a first end region of an anchoring wire 66. The anchoring wire 66 may extend through a lumen or passageway 68 of the stop tube 20 and a second end region may be coupled to the anchoring mechanism 22, for example, the helical screw 26. Optionally, one or more centering inserts 70 may be provided along the length of the anchoring wire 66. For example, one or more inserts 70 may be provided within the can 46 and/or the stop tube 20. The inserts 70 may include an opening/passageway configured to receive the anchor wire 66 to keep the anchor wire 66 centered with respect to the implant 10 and minimize buckling and/or kinking of the anchor wire 66 during the deployment of the implant 10. The inserts 70 may be integrally formed with or a separate element from the can 46 or stop tube 20.

Turning now to FIGS. 5 and 6, one embodiment of the first and second latch pins 60, 62 is illustrated in an uncoupled and coupled position, respectively. The first and second latch pins 60, 62 may each have a generally "C" shaped engagement potion 72a, 72b. At least one of the engagement portions 72a, 72b may define a cavity or recess 74 configured to receive a tab or protrusion 76 of the other engagement portion 72a, 72b as generally illustrated in FIG. 6. The engagement portions 72a, 72b may also have a variety of other configurations configured to form a connection.

The first and second latch pins 60, 62 of the latching mechanism 54 may be held in place in the coupled position by the sleeve 52 as generally illustrated in FIGS. 3, 4 and 7. For example, the sleeve 52 and the first and second latch pins 60, 62 may have a size and/or shape configured to substantially prevent the first and second latch pins 60, 62 from moving relative to one another and to provide rotational and/or lateral stability when the latching mechanism is received within the sleeve. To decouple the latching mechanism 54, the sleeve 52 may be pulled back (i.e., pulled proximally away from the heart) to expose one or more of the first and second latch pins 60, 62. Once at least one of the first and second latch pins 60, 62 is exposed, the delivery wire 64 may be moved (for example, twisted/rotated or the like) to decouple the first and second latch pins 60, 62.

As discussed above, the anchoring mechanism 22 of the implant 10 may also include a helical screw 26 coupled to the anchoring wire 66 and a stop mechanism 78. The helical screw 26 may be configured to be advanced from a retracted position in which the helical screw 26 is substantially disposed entirely within the can 46 as generally illustrated in FIG. 7 to an extended position in which the helical screw 26 is configured to engage the heart tissue as generally illustrated in FIG. 8. The implant 10 may be advanced through the delivery catheter 12 while in the retracted position. Retracting the helical screw 26 within the can 46 while advancing the implant 10 through the delivery catheter 12 may facilitate loading and/or advancing the implant 10 through the delivery catheter 12 by minimizing the likelihood that the anchoring mechanism 22 may become jammed within the lumen 24 of the delivery catheter 12. Alternatively, a portion of the helical screw 26 (for example, the distal most end region) may be disposed beyond the can 46.

The stop mechanism 78 may be configured to control the maximum depth that the helical screw 26 may be extended from the can 46 thereby controlling the maximum depth that the helical screw 26 may be inserted into the native coronary tissue 6 when securing the implant 10. Consistent with at least one embodiment herein, the stop mechanism 78 may comprise a threaded region 80 disposed within the can 46 of the anchoring mechanism 22. The threaded region may 80 may have a thread pitch and size substantially corresponding to a first portion 82 of the helical screw 26. As such, the first portion 82 of the helical screw 26 may be rotated and threaded through the threaded region 82 of the stop mechanism 78 to advance the helical screw 26 out of the can 46 from the retracted position (as generally illustrated in FIG. 7) to the extended position (as generally illustrated in FIG. 8).

The helical screw 26 may also include a second portion 84 having a pitch (for example, but not limited to, a zero pitch) which cannot pass through the threaded region 80. As the anchoring wire 66 is rotated (e.g., from a rotational torque applied to the delivery wire 64 and transmitted through the latching mechanism 54), the first region 82 of the helical screw 26 may be threaded through the stop mechanism 78 until the second region 84 engages (e.g., binds against) the threaded region 80 of the stop mechanism 78. As such, the stop mechanism 78 may be configured to control the maximum depth that the helical screw 26 may be extended from the can 46 thereby controlling the maximum depth that the helical screw 26 may be inserted into the native coronary tissue 6 when securing the implant 10 in the heart 2.

To deliver the implant 10, the first and second latch pins 60, 62 of the latching mechanism 54 may be coupled together as generally illustrated in FIG. 6 and loaded into the distal end region of the sleeve 52 as generally illustrated in FIG. 7. The sleeve 52 may be configured to keep the first and second latch pins 60, 62 of the latching mechanism 54 secured together by generally preventing movement of the first and second latch pins 60, 62 relative to each other. The distal end region of the sleeve 52 (including the first and second latch pins 60, 62) may then be received into the implant 10, for example, into the cavity formed by the garage 36 as generally illustrated in FIGS. 3 and 4. The arrangement/configuration of the garage 36 and the sleeve 52 may provide rotational stability to the first and second latch pins 60, 62 of the latching mechanism 54 when a force or torque is applied to the delivery wire 64.

With distal end of the sleeve 52 and the first and second latch pins 60, 62 of the latching mechanism 54 disposed within the can 36 as generally illustrated in FIGS. 3 and 4, the implant 10 may be loaded into and advanced through the delivery catheter 12 by using a pusher (for example, but not limited to, a low density polyethylene tube or the like). The pusher may be received into the delivery catheter 12 after the implant 10 and may urge the implant 10 through the delivery catheter 12.

The implant 10 may be advanced through the delivery catheter 12 until the anchoring mechanism 22 of the implant 10 is disposed proximate the distal end region of the delivery catheter 12 as generally illustrated FIG. 7. As the implant 10 is advanced through the delivery catheter 12, the sleeve 52 may be maintained around the latching mechanism 54 to ensure that the latching mechanism 54 remains coupled. Additionally, the dimensional tolerances between the garage cavity 58 and the sleeve 52 as well as the latching mechanism 54 and the sleeve 52 may increase the rotational and/or lateral stability of the latching mechanism 54. Once the anchoring mechanism 22 is disposed proximate the distal end region of the delivery catheter 12 and the delivery catheter 12 is in the appropriate location within the heart 1 (for example, but not limited to, proximate the apex of the left ventricle 5), a translational force may be applied to the pusher to urge the anchoring mechanism 22 of the implant 10 (e.g., but not limited to, the can 46) against the native coronary tissue 6 in the heart 1.

A torque may also be applied to the delivery wire 64 and transmitted through the latching mechanism 54 and the anchoring wire 66 causing the helical screw 26 to rotate within the stop mechanism 78 as generally illustrated FIG. 7. The delivery wire 64 may have sufficient flexibility to pass through the delivery catheter 12 while also having sufficient rigidity to resist buckling or kinking under load. According to one embodiment, the delivery wire 64 may include a ⅟₃₂" wire. The translational force applied to the pusher may urge the can 46 against the native coronary tissue 6. As a result, the torque applied to the delivery wire 64 and anchor wire 66 may cause the helical screw 26 of the anchoring mechanism 22 to rotate with respect to the can 46 while keeping the can 46 (and the remainder of the implant 10) substantially stationary.

As the anchoring mechanism 22 is rotated, the helical screw 26 may be advanced from the retracted position to the extended position in which at least a portion of the helical screw 26 is exposed beyond the distal end of the can 46 as generally illustrated in FIG. 8. The dimensional tolerances between the garage cavity 58 and the sleeve 52 as well as the latching mechanism 54 and the sleeve lumen 56 may increase the rotational and/or lateral stability of the latching mechanism 54. Additionally, the centering inserts 70 may increase the rotational and/or lateral stability of the anchoring wire 66 within the implant 10 during rotation of the helical screw 26. The helical screw 26 may be threaded into the tissue of the heart until the second region 84 of the helical screw 26 engages against (e.g., binds) the stop mechanism 78. The stop mechanism 78 may therefore control the maximum depth that the helical screw 26 may be threaded into the native coronary tissue 6 and may reduce the potential of the helical screw 26 puncturing through the opposite side of the heart 1. Additional long-term fixation of the implant 10 may be provided by the pledget 48 disposed about the distal end region of the anchoring mechanism 22.

Once the helical screw 26 of the implant 10 is secured to the native coronary tissue 6, the distal end region of the sleeve 52 may be pulled back (i.e., towards the proximal end of the delivery catheter 12) to expose one or more of the latching pins 60, 62. Once exposed, the delivery wire 64 may be rotated to decouple the latching pins 60, 62 and therefore decouple the delivery wire 64 from the implant 10. The delivery wire 64 (along with the first latching pin 60) may then be pulled back and removed from the implant 10.

Figure 9:
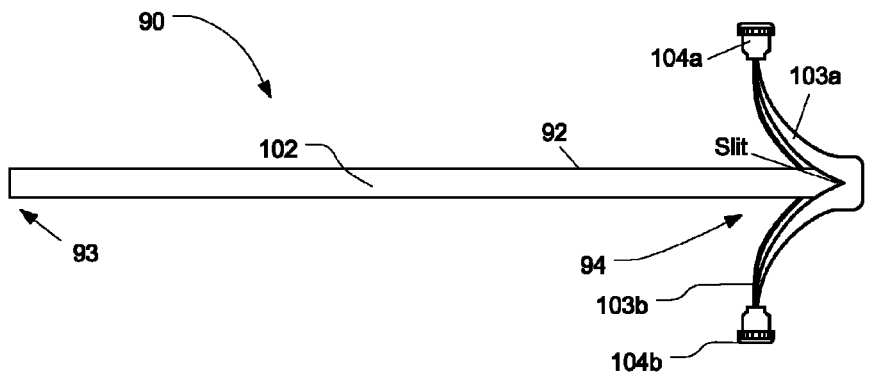
FIG. 9 depicts one embodiment of a loading sheath consistent with the present disclosure.
Figure 10:
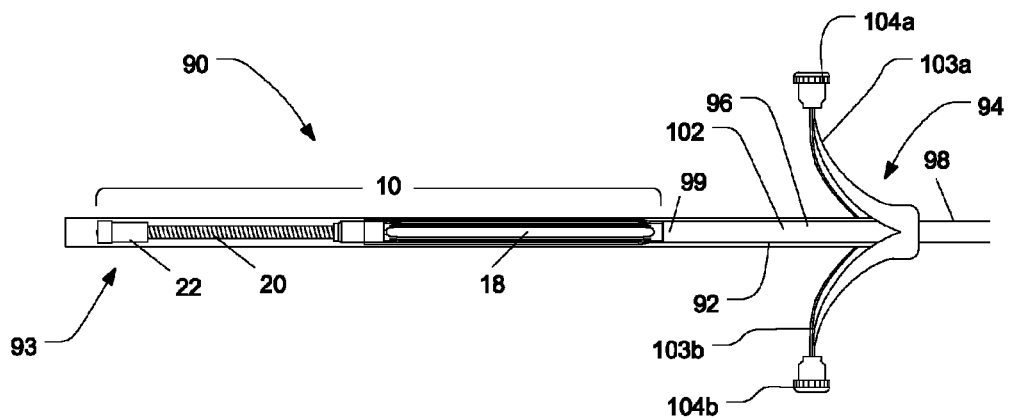
FIG. 10 depicts a cross-sectional view of one embodiment of an implant, a pusher and loading sheath consistent with the present disclosure.

Turning now to FIGS. 9-14, one embodiment of a loading system 90 for loading an implant 10 into the delivery catheter 12 is generally illustrated. As discussed herein, the implant 10 may include a spacer 18 having a diameter which, when expanded, is greater than the diameter of the delivery catheter lumen 24. The loading system 90 may include a loading sheath 92, as generally illustrated in FIG. 9, configured to load the implant 10 into the delivery catheter 12. The loading sheath 92 may include a distal end 93, a proximal end 94 and a hollow shaft or lumen 96. The at least a portion of the implant spacer 18 may be received into the hollow shaft/lumen 96 of the loading sheath 92 as generally illustrated in FIG. 10. The internal dimensions of the lumen loading sheath 96 may be configured to at least partially compress and/or collapse the spacer 18, thereby reducing the cross-section of the implant 10.

Optionally, the lumen 96 of the loading sheath 92 may be configured to receive the entire implant 10 as illustrated. For example, the anchor portion 22 of the implant 10 may be located proximate the distal end 93 of the loading sheath 92. The proximal end 94 of the loading sheath 92 may also be configured receive a portion of a pusher 98, for example, the proximal end region 99 of the pusher 98. As discussed herein, the pusher 98 may be configured to advance the implant 10 through the delivery catheter to the implant 10 site and may include a low density polyethylene tube or the like. The delivery wire 64 may also be disposed within the loading sheath 92 and through the lumen of the pusher 98.

Figure 11:
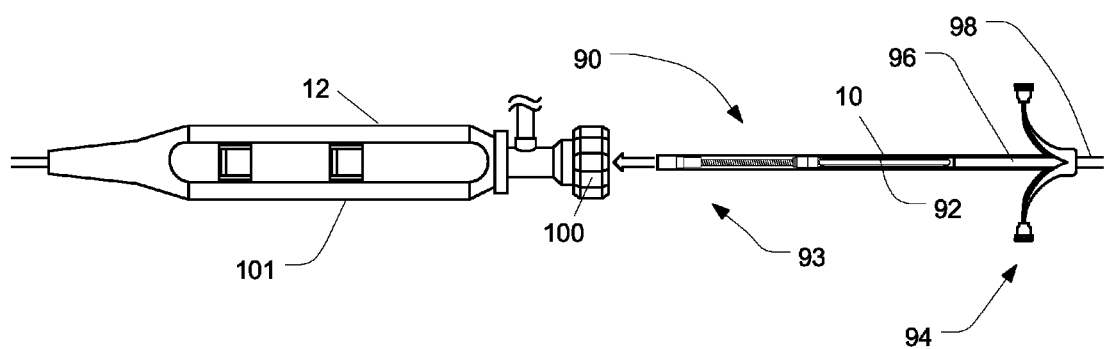
FIGS. 11-14 illustrate one embodiment of loading an implant into a delivery catheter consistent with the present disclosure.
Figure 12:
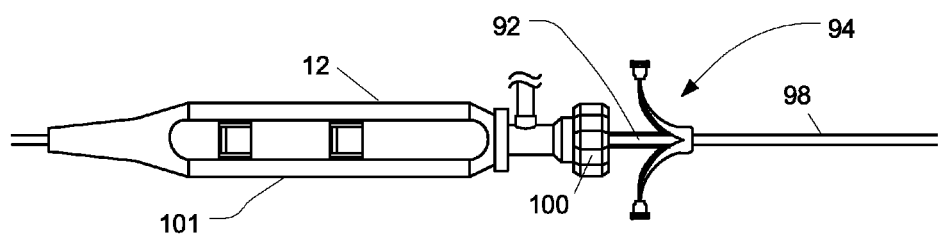

Turning now to FIG. 11, with the implant 10 and pusher 98 received in the lumen 96 of the loading sheath 92, the distal end 93 of the loading sheath 92 may be first advanced through the hemostasis valve 100 of the delivery catheter 12 and optionally into the control handle 101 of the delivery catheter 12 (which is configured to control the position of the distal end of the delivery catheter 12) as generally illustrated in FIG. 12. The loading sheath 92 may be further advanced into the delivery catheter 12 until the entire spacer 18 is received in the delivery catheter 12. Optionally, the loading sheath 92 may be advanced until the proximal end region 94 of the loading sheath 92 is received in the delivery catheter 12. As such, the distal end region of the pusher 98 may also be loaded into the delivery catheter 12 as well the implant 10.

With the implant 10 received within the delivery catheter 12, the loading sheath 92 may be removed from the delivery catheter 12 as well as the implant 10 and the pusher 98. According to one embodiment, the pusher 98 may be held in place and the loading sheath 92 may be pulled distally out of the hemostatsis valve 100 and away from the delivery catheter 12. The loading sheath 92 may then be advanced over the remaining length of the exposed pusher 98. As may be appreciated, however, the pusher 98 may relatively long and other objects of the percutaneous delivery system 1 may prevent the loading sheath 92 from simply sliding off.

Figure 13:
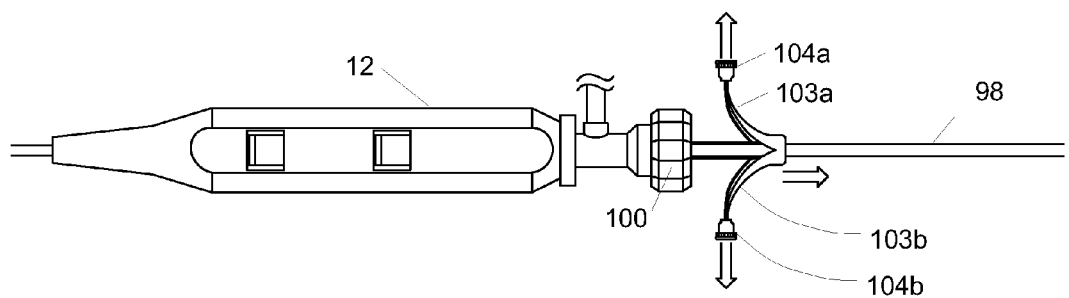
Figure 14:
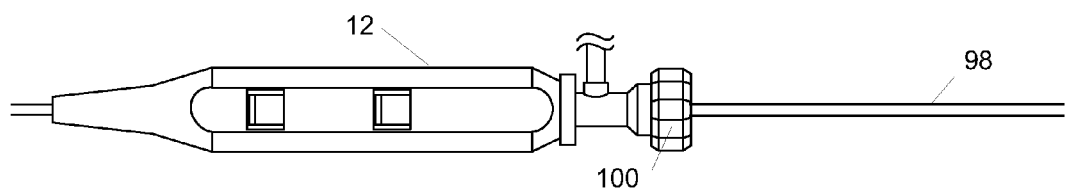

To facilitate the removal of the loading sheath 92, the loading sheath 92 may optionally include a peel-away sheath as generally illustrated in FIGS. 9, 10 and 13. According to this embodiment, the loading sheath 92 may include a longitudinal split, perforation, or the like 102 and optionally one or more (for example, two) tabs 103a, 103b and/or knobs 104a and 104b. Once the implant 10 and/or the pusher 98 are received inside the lumen of the delivery catheter 12, the loading sheath 92 may be removed by holding the pusher 98 substantially stationary and pulling on the two knobs 104a, 104b attached to the tabs 103a, 103b of the loading sheath 92 causing the loading sheath 92 to split in half along its longitudinal axis. With the loading sheath 92 split, it may be easily removed from the pusher 98. As a result, the implant 10 and the pusher 98 may be loaded into the delivery catheter 12 as generally illustrated in FIG. 14.

Figure 15:
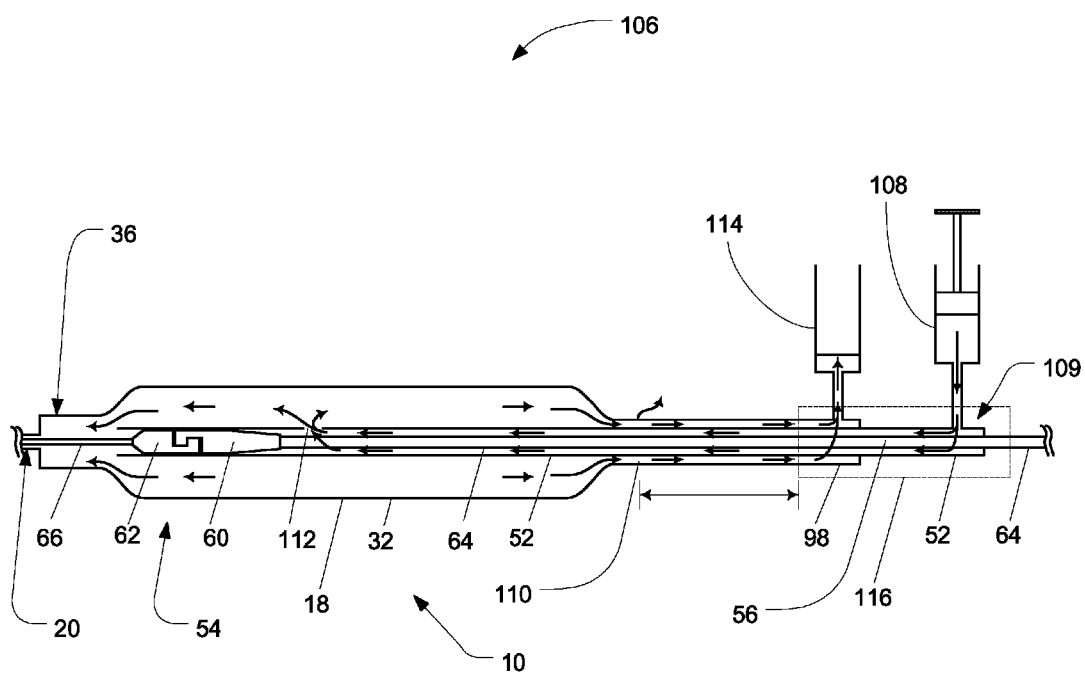
FIG. 15 depicts a schematic diagram illustrating one embodiment of the implant de-airing procedure consistent with the present disclosure.

Turning now to FIG. 15, one embodiment of a de-airing system 106 is generally illustrated. The de-airing system 106 is configured to allow the user (e.g., physician) to remove any air associated with the implant 10 prior to inserting the implant 10 into the delivery catheter 12. If entrapped air from the percutaneous delivery system is allowed to be introduced into the patient's cardiovascular system, the air may be travel to the patient's brain or other parts of the patient's body where it may cause serious bodily harm and/or death (for example, due to blood clotting or the like).

According to at least one embodiment herein, the de-airing system 106 may include a fluid (such as, but not limited to, a saline solution or the like) which may be injected around the implant 10 to flush away and/or remove any entrapped air before the implant 10 is inserted into the delivery catheter 12. The de-airing system 106 may include a first reservoir 108 of fluid which may be configured to be fluidly coupled to the lumen 56 of the sleeve 52, for example, about the proximal end 109 of the sleeve 52. The sleeve 52 may be disposed within a lumen 110 of the pusher 98 which may be substantially abutting against a distal end of the implant 10. The fluid may be injected into the lumen 56 of the sleeve 52 where it may flow through the sleeve 52 and around delivery wire 64 and the latching mechanism 54. A portion of the fluid may also flow pass the latching mechanism 54, through the garage 36 and stop tube 20, around anchor wire 66, into the can 46 and through the threaded region 80 and helical screw 26, and out the distal end of the implant 10.

The sleeve 52 may also include one or more openings, slots, apertures 112 or the like configured allow some of the fluid to pass out of the sleeve 52 and fill spacer 18. The fluid may then flow from the spacer 18 into the lumen 110 of the pusher 98 back to a second reservoir 114 fluidly coupled to the pusher 98. As may be appreciated, the fluid flowing through the de-airing system 106 may remove any air entrapped around the implant 10. As a result, the implant 10 may be loaded into the delivery catheter 12 without introducing any unwanted air into the patient's cardiovascular system.

Figure 16:
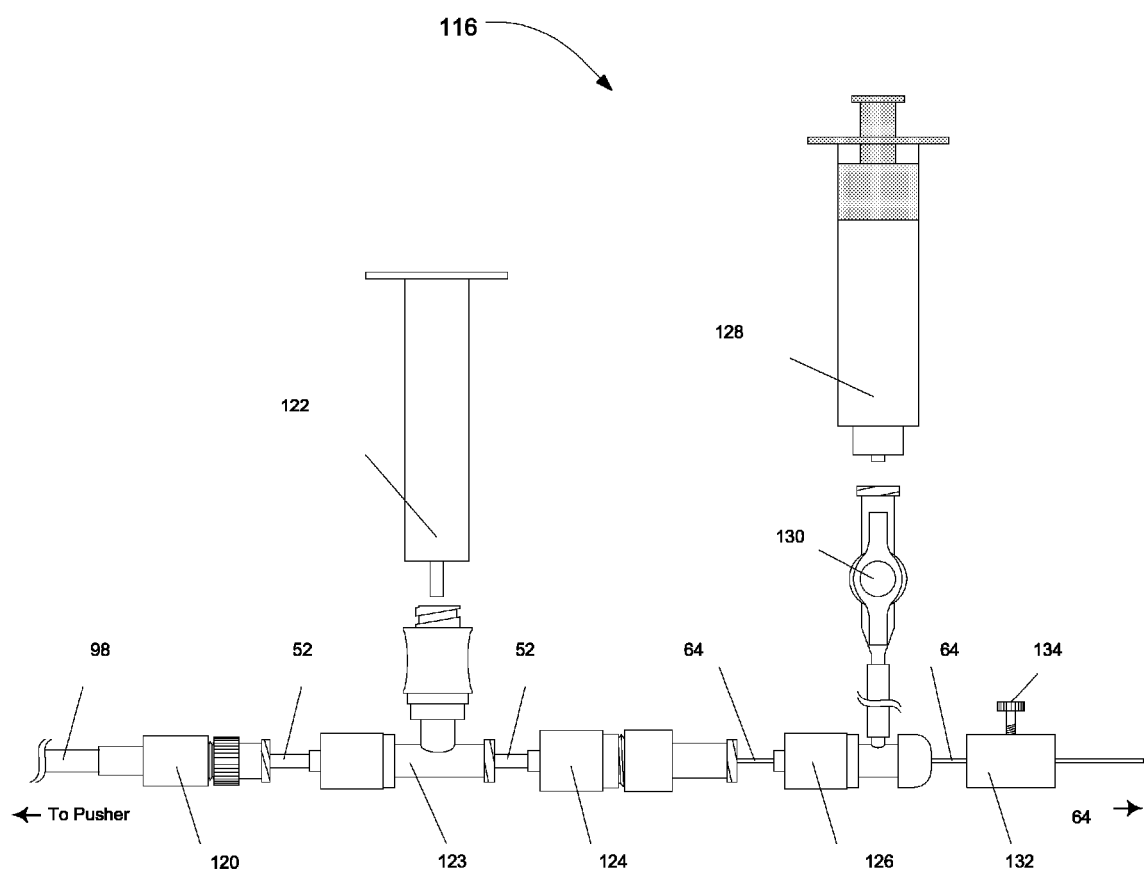
FIG. 16 depicts a schematic diagram illustrating one embodiment of the de-airing driver handle system consistent with the present disclosure.

Turning now to FIG. 16, one embodiment of a de-airing driver handle system 116 is illustrated in an exploded or unassembled view. The de-airing driver handle system 116 may include a de-airing system and/or a driver handle. The de-airing system may be configured to remove air from the implant 10 prior to inserting the implant 10 into the delivery catheter 12 as discussed herein while the driver handle may be configured to manage the position of the sleeve 52 and decoupling of the latching mechanism 54 as well as to enable rotation of the helical screw 26 into the native coronary tissue 6 upon deployment of the implant 10.

The de-airing driver handle system 116 may include a pusher fitting 120 configured to terminate the proximal end of the pusher 98. The pusher fitting 120 may be configured to allow the sleeve 52 to be disposed within the lumen 110 of the pusher 98 and to extend beyond the proximal end of the pusher 98. For example, the pusher fitting 120 may a compression fitting or the like. A fluid receiving reservoir 122 may be fluidly coupled to the pusher fitting 120 and may be configured to receive fluid flowing from the implant 10 and the pusher lumen 110. According to at least one embodiment, the fluid receiving reservoir 122 may include a fitting including a needle-less injector port 123 or the like.

A sleeve fitting 124 may also be coupled to the fluid receiving reservoir 122 for terminating the proximal end of the sleeve 52. The sleeve fitting 124 may be configured to allow the delivery wire 64 to be disposed within the lumen 56 of the sleeve 52 and to extend beyond the proximal end of the sleeve 52. For example, the sleeve fitting 124 may include a compression fitting or the like. A fluid injection reservoir 126 may be fluidly coupled to the sleeve fitting 124 and may be configured to inject fluid into lumen 54 of the sleeve 52 where it ultimately flows around the implant 10 and into the pusher 98 as discussed herein. According to at least one embodiment, the fluid injection reservoir 126 may include a fitting configured to be fluidly coupled to a syringe 128 or the like and the sleeve 52. The fitting may be configured to allow the delivery wire 64 to sealingly pass through. Optionally, a valve 130 (such as, but not limited to, a stopcock or the like) may be provided to further regulate the flow of fluid form the fluid injection reservoir 126. A drive knob 132 or the like may be coupled to the delivery wire 64 to rotate the delivery wire 64 and, ultimately, the helical screw 26 of the anchor mechanism 22. The drive knob 132 may include a set-screw, clamp or the like 134 configured to allow the drive knob 132 to be releasably coupled to the delivery wire 64.

It may be appreciated that one embodiment of the functional components of the de-airing driver handle system 116 have been illustrated and described. The various components may be combined and/or split into one or more systems. For example, the various fittings may be combined into a single driver handle device to facilitate their use.

Figure 17:
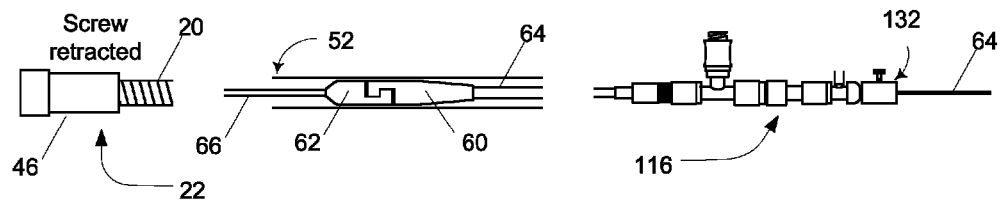
FIGS. 17-22 illustrate one embodiment for delivering an implant consistent with the present disclosure.

Turning now to FIGS. 17-22, one embodiment illustrating the procedure for anchoring the implant 10 into the native coronary tissue 6 is generally illustrated. The implant 10 may be advanced through the delivery catheter 12 by applying a translational force to the pusher 98 and against the implant 10. As the implant 10 along with the entire pusher 98 assembly (de-airing driver handle system 116) is advanced forward through the delivery catheter 12, the can 46 of the implant 10 may emerge from the distal end of the delivery catheter 12 and may be urged/biased against the native coronary tissue 6 (for example, against the wall of the left ventricle 5 proximate the apex) as generally illustrated in FIGS. 1 and 17. As can be seen, the distal end region of the sleeve 52 may be disposed substantially around the latching mechanism 54 including the first and second latching pins 60, 62. In addition, the anchoring mechanism 22 may be disposed in the retracted position in which the helical screw 26 may be disposed within the can 46.

Figure 18:
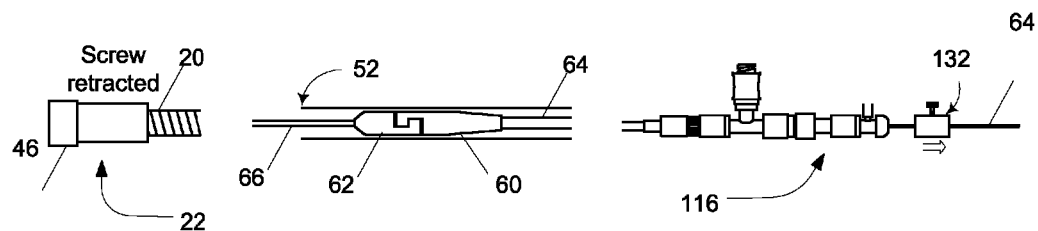

Turning now to FIG. 18, the set-screw 134 on the driver knob 132 may optionally be loosened and the drive knob 132 may be moved back from the proximal end of the de-airing handle system 116 along the delivery wire 64 and retightened to allow the helical screw 26 to be advanced during the subsequent steps. For example, the drive knob 132 may be moved back approximately 1 cm.

Figure 19:
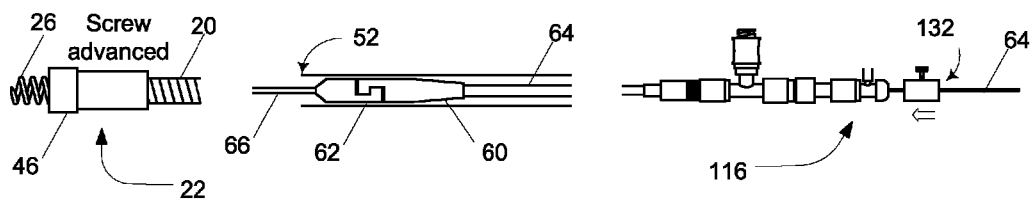

With the can 46 against the native coronary tissue 6 and the driver knob 132 moved back from the de-airing handle system 116, the driver knob 132 may be rotated and urged forward to cause the delivery wire 64 to be rotated as generally illustrated in FIG. 19. The torque may be transmitted through the latching mechanism 54 causing the anchoring wire 66 and ultimate the helical screw 26 to rotate. Additionally, a translational force may be applied to the pusher 98 to urge the can 46 of the implant 10 against the native coronary tissue 6 and generally prevent rotation of the can 46. The sleeve 52 may be disposed about the first and second latching pins 60, 62 and, along with the garage 36, may be configured to provide lateral and rotational stability to the latching mechanism 54 as described herein. Additionally, one or more centering inserts 70 may also provide additional lateral and rotational stability.

The first portion 82 of the helical screw 26 may rotate within the threaded region 80 to advance the helical screw 26 beyond the distal end of the can 46 and into the native coronary tissue 6. The helical screw 26 may be advanced beyond the distal end of the can 46 until the second portion engages 84 against or binds with the threaded region 80. As a result, the maximum depth that the helical screw 26 may be advanced into the native coronary tissue 6 may be controlled and puncturing of the heart wall 1 may be avoided.

Figure 20:
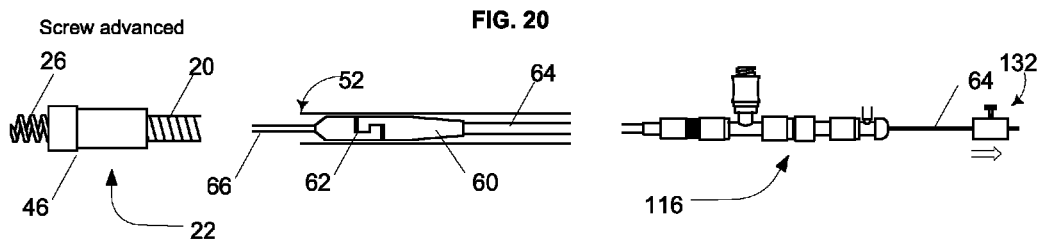

Turning now to FIG. 20, the set-screw 134 on the driver knob 132 may optionally be loosened and the drive knob 132 may be moved back from the proximal end of the de-airing handle system 116 along the delivery wire 64 and retightened to allow the latching mechanism 54 to be decoupled. For example, the drive knob 132 may be moved back approximately 2 inches.

Figure 21:
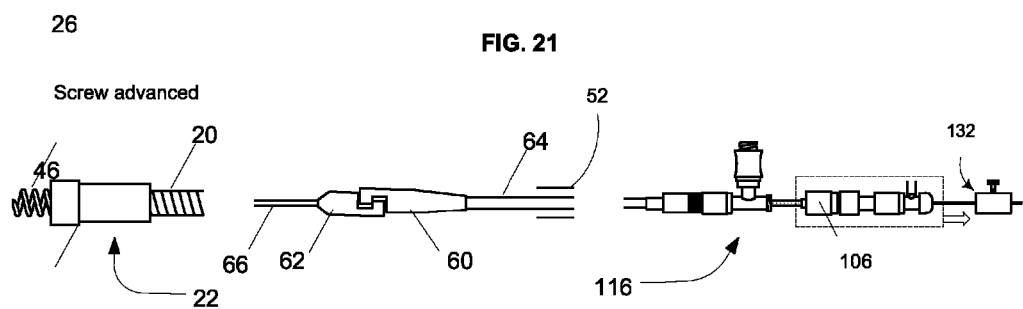

To decouple the latching mechanism 54, the sleeve 52 fitting of the de-airing handle system 116 may be disconnected and the sleeve 52 may be retracted (i.e., moved proximally away from the implant 10) as generally illustrated in FIG. 21. As the sleeve 52 is retracted, one or more of the latching pins 60, 62 may be exposed from the distal end region of the sleeve 52. The latching pins 60, 62 may still be loosely coupled at this point.

Figure 22:
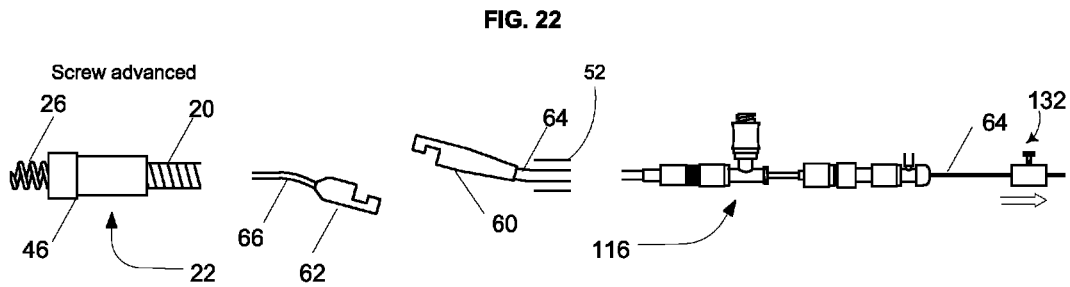

Turning now to FIG. 22, the delivery wire 64 may also be retracted. Retracting the delivery wire 64 may fully disengage/decouple the first and second latching pins 60, 62. The disengagement of the latching mechanism 54 may be seen on fluoroscopy or the like and may also be felt by the physician (the delivery wire 64 will feel loose when disengaged/decoupled). The sleeve 52 and the delivery wire 64 may be retracted out of the implant 10 (not shown). The pusher 98 may be held against the implant 10 and the delivery catheter 12 may be retracted to further deploy the implant 10.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure as determined by the claims when interpreted in accordance with breadth to which they are fairly, legally and equitably entitled.

What is claimed is:

1. A method of delivering an implant within a heart, said implant including a shaft, a spacer configured to interact with at least a portion of at least one cusp of a heart valve to at least partially restrict a flow of blood through said heart valve in a closed position, and at least one anchor mechanism coupled to a first end region of said shaft, said method comprising:
   providing a delivery wire having a first latch pin;
   coupling said first latch pin to a second latch pin disposed within said implant;
   advancing a distal end of a sleeve over said first and said second latch pins to prevent movement of said first and said second latch pins;
   percutaneously delivering a catheter proximate said heart;
   loading said implant and said distal end of said sleeve into said catheter; and
   advancing said implant and said distal end of said sleeve through said catheter.

2. The method of claim 1, further comprising rotating said delivery wire and transmitting torque through said first and said second pins to cause said anchoring mechanism to engage tissue within said heart.

3. The method of claim 2, further comprising:
   retracting said distal end of said sleeve to expose at least one of said first and second pins; and
   decoupling said first and said second latching pins.

4. The method of claim 1, wherein said implant further comprises garage configured to couple said spacer to said shaft, said garage defining a cavity configured to receive said distal end region of said sleeve to increase rotational and translational stability of said sleeve.

5. The method of claim 1, further comprising de-airing the implant prior to loading said implant into said catheter.

6. The method of claim 1, further comprising loading a distal end of a pusher into said catheter.

7. The method of claim 6, wherein said pusher and said implant are loaded into said catheter with a loading system comprising a loading sheath.

8. The method of claim 1, wherein said percutaneously delivering comprises advancing said implant through said catheter by applying a translational force to said pusher.

9. The method of claim 1, wherein said anchoring mechanism comprises a cavity configured to at least partially receive a helical screw, the method further comprising rotating said helical screw to advance said helical screw into tissue of said heart.

10. The method of claim 9, wherein said anchoring mechanism further comprises a threaded region secured within said cavity, said threaded region having a thread pitch and size substantially corresponding to a first threaded region of said helical screw.

* * * * *